US011471882B2

(12) United States Patent
Strong et al.

(10) Patent No.: US 11,471,882 B2
(45) Date of Patent: Oct. 18, 2022

(54) LATERAL FLOW ASSAY DEVICE

(71) Applicant: Bio-Rad Laboratories, Inc., Hercules, CA (US)

(72) Inventors: William Strong, El Cerrito, CA (US); Clayton T. McKee, Davis, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 343 days.

(21) Appl. No.: 16/867,265

(22) Filed: May 5, 2020

(65) Prior Publication Data
US 2020/0261905 A1    Aug. 20, 2020

Related U.S. Application Data

(63) Continuation of application No. 15/818,340, filed on Nov. 20, 2017, now Pat. No. 10,688,487.

(60) Provisional application No. 62/425,839, filed on Nov. 23, 2016.

(51) Int. Cl.
*G01N 33/558*    (2006.01)
*B01L 3/00*    (2006.01)
*G01N 33/543*    (2006.01)

(52) U.S. Cl.
CPC ...... *B01L 3/5023* (2013.01); *G01N 33/54386* (2013.01); *G01N 33/558* (2013.01); *B01L 2300/069* (2013.01); *B01L 2300/0809* (2013.01); *B01L 2300/0825* (2013.01); *B01L 2300/0829* (2013.01); *B01L 2300/0887* (2013.01); *B01L 2300/126* (2013.01); *B01L 2300/165* (2013.01); *B01L 2400/0406* (2013.01); *B01L 2400/0475* (2013.01)

(58) Field of Classification Search
None
See application file for complete search history.

(56) References Cited

U.S. PATENT DOCUMENTS

| | | |
|---|---|---|
| 4,981,785 A | 1/1991 | Nayak |
| 4,981,786 A | 1/1991 | Dafforn et al. |
| 5,198,193 A | 3/1993 | Bunce et al. |
| 5,744,096 A | 4/1998 | Jones et al. |
| 5,914,273 A | 6/1999 | Kok |
| 6,436,722 B1 | 8/2002 | Clark et al. |
| 7,238,519 B2 | 7/2007 | Belief et al. |
| 8,501,495 B2 | 8/2013 | Yao et al. |
| 8,507,260 B2 | 8/2013 | Alajem et al. |
| 9,101,927 B2 | 8/2015 | Alajem et al. |
| 9,671,402 B2 | 6/2017 | McKee |
| 2007/0134811 A1 | 6/2007 | Takeuchi et al. |
| 2010/0233708 A1 | 9/2010 | Mehra et al. |
| 2010/0239459 A1 | 9/2010 | Alajem et al. |

(Continued)

FOREIGN PATENT DOCUMENTS

| | | |
|---|---|---|
| CN | 102076415 A | 5/2011 |
| EP | 1044372 B1 | 9/2003 |

(Continued)

OTHER PUBLICATIONS

The International Search Report and Written Opinion from Application No. PCT/US2017/062516, dated Jan. 23, 2018.

(Continued)

*Primary Examiner* — Rebecca M Giere
(74) *Attorney, Agent, or Firm* — Kilpatrick Townsend and Stockton LLP

(57) ABSTRACT

Lateral flow devices, methods and kits for performing lateral flow assays are provided.

20 Claims, 14 Drawing Sheets

(56) References Cited

U.S. PATENT DOCUMENTS

| | | |
|---|---|---|
| 2011/0189792 A1 | 8/2011 | Reinhartz et al. |
| 2013/0164193 A1 | 6/2013 | Semenov et al. |
| 2016/0038935 A1 | 2/2016 | Alajem et al. |
| 2016/0291009 A1 | 10/2016 | Kim et al. |
| 2017/0191997 A1 | 7/2017 | McKee et al. |
| 2018/0024129 A1 | 1/2018 | Strong |

FOREIGN PATENT DOCUMENTS

| | | |
|---|---|---|
| EP | 2910946 A1 | 8/2015 |
| WO | 99/36776 A1 | 7/1999 |
| WO | 2006/080021 A2 | 8/2006 |
| WO | 2011/014673 A1 | 2/2011 |
| WO | 2013/095729 A1 | 6/2013 |
| WO | 2015/160996 A1 | 10/2015 |
| WO | 2017/109775 A1 | 6/2017 |

OTHER PUBLICATIONS

Partial European Search Report in EP Appln. 17874590.7 dated Mar. 30, 2020; 16 pages.
Extended European Search Report in EP Application 17874590.7 dated Jun. 4, 2020; 15 pages.

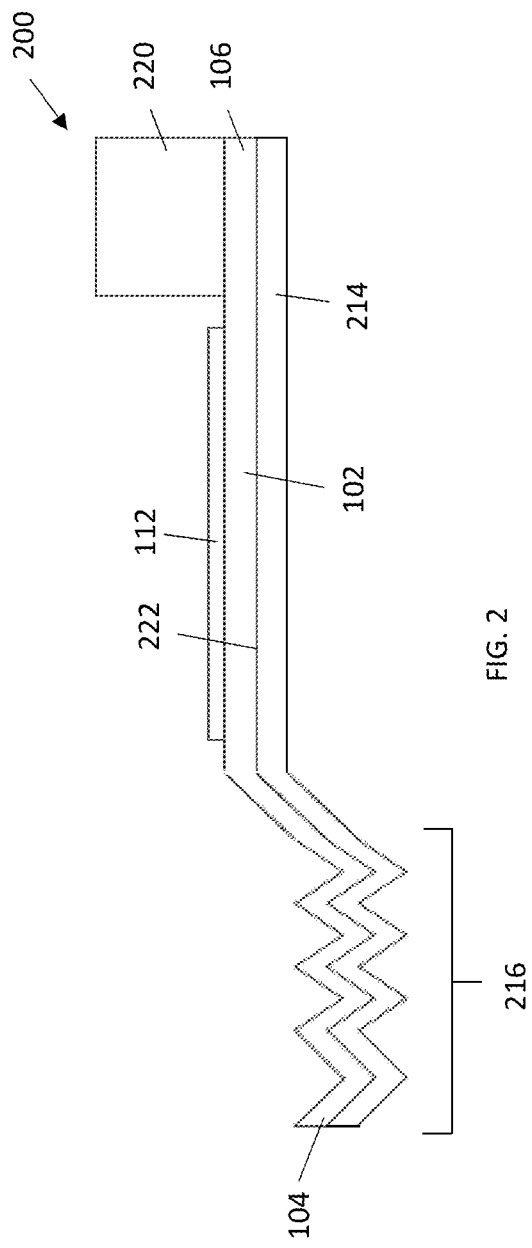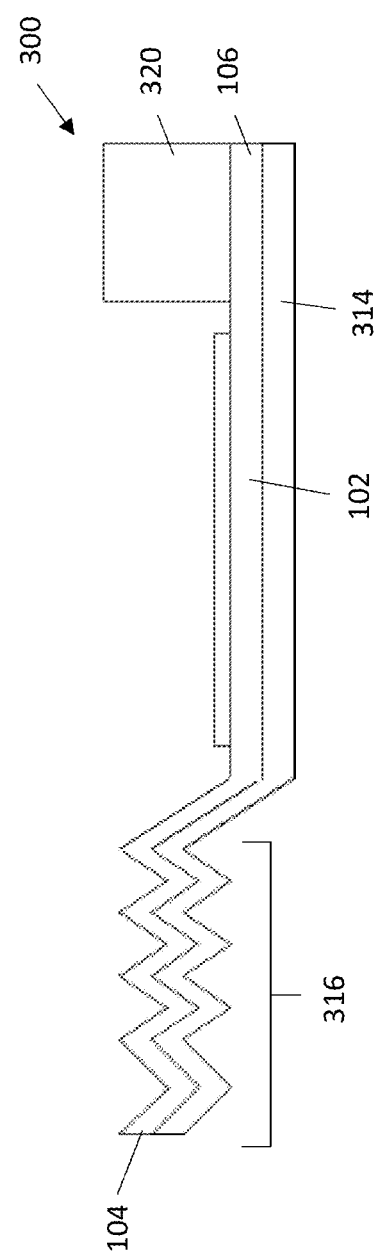
FIG. 2
FIG. 3

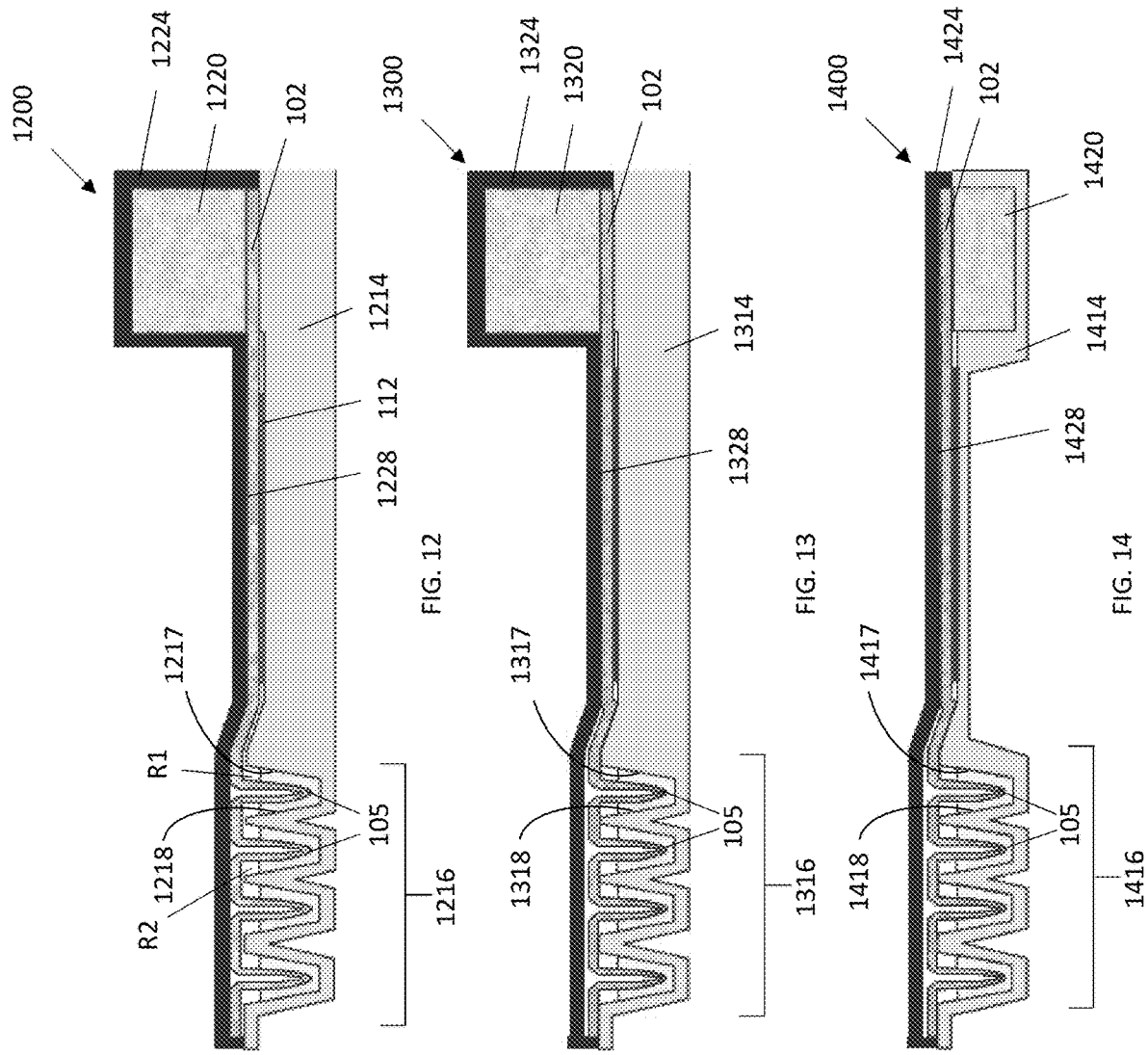

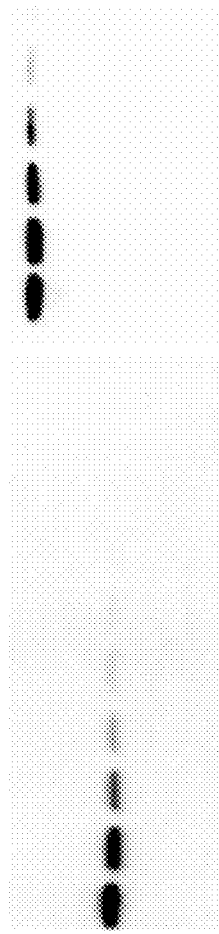
FIG. 18B
FIG. 18A
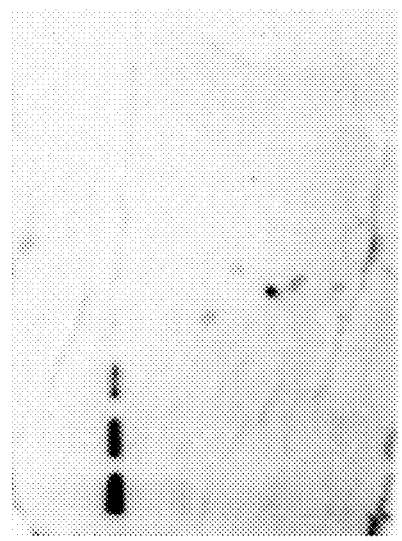
FIG. 18C

LATERAL FLOW ASSAY DEVICE

This application is a continuation of U.S. application Ser. No. 15/818,340 filed Nov. 20, 2017, which claims the benefit of U.S. Application 62/425,839 filed on Nov. 23, 2016, each of which is hereby incorporated by reference in its entirety.

BACKGROUND

Methods for detection of immobilized analytes are commonly employed in the biological sciences. For example, traditional blotting (e.g., Southern, northern, western, far western, eastern, vacuum, middle eastern, eastern-western, and far-eastern blotting, etc.) can be used to detect analytes immobilized on a substrate or membrane or in a matrix (e.g., in agarose or acrylamide). In general, such blotting techniques involve immobilization of the analyte(s) to be detected and contacting the analyte(s) with a binding agent (e.g., an antibody). Blotting also usually involves multiple washing steps and/or blocking steps between immobilization and final detection. Such washing and blocking steps consume a practitioner's limited time and/or reagents and can be a source of error and irreproducibility.

SUMMARY

Provided herein are lateral flow assay devices and methods of using such devices.

In an embodiment, the lateral flow device comprises a wicking pad composed of a porous material, the wicking pad having a planar region for contacting a substrate (e.g., a Western blot) comprising immobilized analytes (e.g., proteins); and wherein the wicking pad has a first end, a second end and two lateral edges; a base comprising two or more reservoirs spatially separated from each other, wherein each of the reservoirs receives and is in fluid communication with the first end of the wicking pad; and a pump comprising an absorbent pad located on the second end of the wicking pad. In certain embodiments, the lateral flow device comprises a wicking pad composed of a porous material, the wicking pad having a planar region comprising immobilized binding agents; and wherein the wicking pad has a first end, a second end and two lateral edges; a base comprising two or more reservoirs spatially separated from each other, wherein each of the reservoirs receives and is in fluid communication with the first end of the wicking pad; and a pump comprising an absorbent pad contacting the second end of the wicking pad. In some embodiments, the lateral flow device further comprises a cover. In some embodiments, each reservoir has a longest dimension perpendicular to the lateral edges of the wicking pad. In certain embodiments, one or more reservoirs have a longer dimension parallel to the lateral edges of the wicking pad.

In some embodiments, each of the reservoirs is a depression. In some embodiments, a lowest point of one or more of the reservoirs is located below, above, or in the plane of the planar region for contacting the substrate. In certain embodiments, a lowest point of all of the reservoirs is located on the same plane. In some embodiments, each of the reservoirs comprises a length, a width and a depth. In some embodiments, each of the reservoirs spans a width of the wicking pad. In certain embodiments, a cross-section of each of the reservoirs has a shape selected from the group consisting of a v, a semicircle, an oval, a u, a rectangle, a square, and a trapezoid. In some embodiments, each of the reservoirs comprises a wall having a slope. In some embodiments, the reservoirs are attached to each other on at least one side. In certain embodiments, the base is formed from molded plastic. In some embodiments, the reservoirs comprise two or more sets of reservoirs spatially separated from and adjacent to each other on a width axis of the lateral flow device.

In some embodiments, at least a part of the wicking pad is in intimate contact with or is bonded to the base. In certain embodiments, at least a part of the wicking pad is in intimate contact with or is bonded to a cover. In some embodiments, the cover comprises at least two projections each of which project into a different reservoir. In some embodiments, each of the projections is a blade spanning the width of the reservoir into which the blade projects. In certain embodiments, at least a portion of the wicking pad follows the contours of and is bonded to each of the projections. In some embodiments, the wicking pad is not bonded to the base or the cover and each of the projections urge portions of the wicking pad into a different reservoir when the cover is placed onto the device. In certain embodiments, at least two portions of the wicking pad are formed into protrusions each of which project into a different reservoir when the cover is placed onto the device.

In some embodiments, the wicking pad and the pump are dry. In some embodiments, the wicking pad is wet. In some embodiments, the analytes are proteins. In some embodiments, the pump contacts an upper surface or a lower surface of the second end of the wicking pad.

In some embodiments, the wicking pad and the pump are formed of at least one absorbent material selected from the group consisting of glass fiber, cotton, cellulose, a cellulose fiber derivative, sintered glass, sintered polymer, sintered metal, and a synthetic polymer. In some embodiments, the substrate is selected from the group consisting of a membrane, glass, plastic, silicon, metal, and metal oxide. In certain embodiments, the membrane is formed of at least one material selected from the group consisting of nitrocellulose, polyvinylidene fluoride, nylon, and polysulfone. In some embodiments, the plastic is selected from the group consisting of polyethylene terephthalate, polypropylene, polystyrene, and polycarbonate.

Also provided are methods of performing lateral flow assays. In some embodiments, the method comprises providing a lateral flow device as described above or elsewhere herein in which the wicking pad is in intimate contact or is bonded at least in part to the base; optionally applying running buffer to the wicking pad; applying a substrate comprising proteins (e.g., a western blot) to the planar region for contacting the substrate; applying a different reagent solution to each of the reservoirs; and allowing lateral flow of the reagent solutions from the reservoirs to the pump such that each of the reagents in the reagent solutions is sequentially transported in the wicking pad and is contacted to the proteins on the substrate. In some embodiments, the reagent solutions are applied to each of the reservoirs starting with a reservoir closest to the planar region for applying the substrate.

In some embodiments in which the device has a cover sealed to the base, the method further comprises removing the cover and applying running buffer and the substrate to the wicking pad; applying a different reagent solution to each of the reservoirs; and placing the cover on the base while allowing lateral flow of the reagent solutions from the reservoirs to the pump.

In some cases, the method comprises providing a lateral flow device as described above or elsewhere herein in which the wicking pad is in intimate contact or is bonded at least in part to the cover; removing the cover from the base;

optionally applying a lateral flow buffer to the wicking pad; contacting the substrate comprising proteins to the planar region of the wicking pad for contacting the substrate; applying a different reagent solution to each of the reservoirs starting with a reservoir closest to the planar region for applying the substrate; contacting each reagent solution with the first end of the wicking pad by placing the cover on the base; and allowing lateral flow of the reagent solutions from the reservoirs to the pump such that each of the reagents in the reagent solutions is sequentially transported in the wicking pad and is contacted to the proteins on the substrate. In some embodiments, the contacting each reagent solution step comprises urging different portions of the first end of the wicking pad into each of the reagent solutions with projections. In certain embodiments, the contacting each reagent step comprises dipping the different portions of the first end of the wicking pad bonded to the projections into the reagent solutions. In some embodiments, the contacting each reagent step comprises dipping at least two protrusions near the first end of the wicking pad into the reagent solutions.

In some embodiments, the method comprises providing a lateral flow device as described above or elsewhere herein in which the wicking pad is in intimate contact or is bonded at least in part to the cover; removing the cover from the base; optionally applying a lateral flow buffer to the wicking pad; contacting the substrate comprising proteins to the planar region of the wicking pad for contacting the substrate; positioning the cover on the base, thereby placing the first end of the wicking pad into each of the reservoirs; applying a different reagent solution to each of the reservoirs starting with a reservoir closest to the planar region for applying the substrate such that each reagent solution contacts the different portion of the first end of the wicking pad; and allowing lateral flow of the reagent solutions from the reservoirs to the pump such that each of the reagents in the reagent solutions is sequentially transported in the wicking pad and is contacted to the proteins on the substrate. In some embodiments, the placing step comprises placing a projection bonded to the wicking pad into each of the reservoirs. In certain embodiments, the placing step comprises urging the different portion of the first end of the wicking pad into each of the reservoirs with a projection. In some embodiments, the placing step comprises placing a protrusion formed from the wicking pad into each of the reservoirs. In some embodiments, the applying a different reagent solution to each of the reservoirs step comprises applying the reagent solution through a port in each of the reservoirs or in the cover.

In some embodiments, the different reagent solutions are applied to the reservoirs sequentially or simultaneously. In some embodiments, the contacting the substrate comprising proteins to the planar region of the wicking pad for contacting the substrate step comprises contacting an upper surface or a lower surface of the wicking pad.

In some embodiments, the allowing lateral flow step comprises allowing primary antibodies from a first reagent solution in a first reservoir to bind to their target proteins, if present, on the substrate, followed by allowing a first wash solution from a second reagent solution in a second reservoir to remove unbound primary antibodies from the substrate. In some embodiments, the allowing lateral flow step further comprises allowing secondary antibodies or a secondary detection reagent from a third reagent solution in a third reservoir to contact the primary antibodies bound to their target proteins, if present, on the substrate. In some embodiments, the allowing lateral flow step further comprises allowing a second wash solution from a fourth reagent solution in a fourth reservoir to remove unbound secondary antibodies from the substrate.

In some embodiments, the volume of the second wash solution is at least twice the volume of the third reagent solution having the secondary antibody. In certain embodiments, the method further comprises following binding of the primary antibodies to the target proteins if present, optionally following contact of secondary antibodies or secondary detection reagents to the primary antibodies, optionally removing the substrate, and detecting the binding of the primary antibodies to the target proteins if present.

In certain embodiments, the method comprises providing a lateral flow device as described above or elsewhere herein in which binding agents are immobilized on a planar region of the wicking pad; optionally applying a lateral flow buffer to the wicking pad; applying a different solution to at least two of the reservoirs starting with a reservoir closest to the planar region of the wicking pad comprising immobilized binding agents; and allowing lateral flow of the solutions from the reservoirs to the pump such that the solutions are sequentially transported in the wicking pad and are contacted to the proteins immobilized on the wicking pad. In some embodiments in which the device has a cover attached to the base, the method further comprises removing the cover; optionally applying lateral flow buffer to the wicking pad; applying a different solution to each of the reservoirs starting with the reservoir closest to the planar region of the wicking pad having immobilized binding agents; and placing the cover on the base while allowing lateral flow of the different solutions from the reservoirs to the pump.

In some embodiments, the method comprises providing a lateral flow device as described above or elsewhere herein in which binding agents are immobilized on a planar region of the wicking pad and in which the wicking pad is in intimate contact or is bonded at least in part to the cover; removing the cover from the base; optionally applying a lateral flow buffer to the wicking pad; applying a different solution to each of the reservoirs starting with a reservoir closest to the planar region of the wicking pad having immobilized binding agents; contacting each solution with the first end of the wicking pad by placing the cover on the base; and allowing lateral flow of the solutions from the reservoirs to the pump such that the solutions are sequentially transported in the wicking pad and are contacted to the binding agents immobilized on the wicking pad. In some embodiments, the contacting each solution step comprises urging different portions of the first end of the wicking pad into each of the solutions with projections. In some embodiments, the contacting each solution step comprises dipping the different portions of the first end of the wicking pad bonded to the projections into the solutions. In some embodiments, the contacting each solution step comprises dipping at least two protrusions near the first end of the wicking pad into the solutions.

In some embodiments, the method comprises providing a lateral flow device as described above or elsewhere herein in which binding agents are immobilized on a planar region of the wicking pad and in which the wicking pad is in intimate contact or is bonded at least in part to the cover; removing the cover from the base; optionally applying a lateral flow buffer to the wicking pad; positioning the cover on the base, thereby placing the first end of the wicking pad into each of the reservoirs; applying a different solution to each of the reservoirs starting with a reservoir closest to the planar region having immobilized binding agents such that each solution contacts the different portion of the first end of the wicking pad; and allowing lateral flow of the solutions from the reservoirs to the pump such that each of the solutions is sequentially transported in the wicking pad and is contacted to the binding agents on the substrate. In some embodiments, the placing step comprises placing a projection bonded to the wicking pad into each of the reservoirs. In some embodiments, the placing step comprises urging the different portion of the first end of the wicking pad into each of the reservoirs with a projection. In certain embodiments, the placing step comprises placing a protrusion formed from the wicking pad into each of the reservoirs. In some embodiments, the applying a different solution to each of the reservoirs step comprises applying each of the solutions through a port in each of the reservoirs or in the cover.

In some embodiments in which binding agents are immobilized on a planar region of the wicking pad, the solution is a sample having an analyte (and optionally, a control protein) therein or a reagent solution having a reagent therein. In some embodiments, the different solutions are applied to the reservoirs sequentially or simultaneously. In some embodiments, the allowing lateral flow step comprises allowing the analytes from the sample in a first reservoir to bind to at least one binding agent immobilized on the wicking pad, followed by allowing a first wash solution in a second reservoir to remove unbound material from the wicking pad. In certain embodiments, the allowing lateral flow step comprises allowing the analyte, if present, to bind to a reversibly immobilized labeled first primary antibody (e.g., a primary antibody conjugate) followed by allowing the complexed analyte to bind to an unlabeled second primary antibody irreversibly immobilized downstream from the first primary antibody. In some embodiments, the method further comprises following binding of the analyte, if present, to the first primary antibody and the second primary antibody, and detecting the binding of the analyte, if present, to the first and second primary antibodies (e.g., detecting the analyte sandwiched between the first and second primary antibodies).

In certain embodiments, the methods further comprise applying a substantially uniform pressure to the pump.

Also provided is a kit for performing lateral flow. In some embodiments, the kit comprises the lateral flow device as described above and elsewhere herein. In some embodiments, the kit includes a plurality of absorbent pads for use as a pump, all of which are described herein. In some embodiments, the kit includes reagents (e.g., binding agents including labeled primary antibody or primary and secondary antibodies, wash solution, and/or running buffer) provided as solutions to be applied to the reservoirs by the end-user. In certain embodiments, some or all of the reagents are dried onto the wicking pad in the portions of the wicking pad in fluid communication with each of the reservoirs of the device.

In some embodiments, the kit further includes running buffer for performing lateral flow and optionally includes blocking agents (e.g., bovine serum albumin, non-fat dried milk, or casein), surfactants (e.g., Tween 20 or Triton X-100), protein aggregation modifying agents as described herein, macromolecular crowding agents (e.g., dextran, polyethylene glycol and/or Ficoll), density agents and/or agents to promote even flow of reagents and/or promote reaction to molecules on the substrate and minimize background on the substrate. The additional agents can be provided in the kit as a solid or in liquid form. In some embodiments, the kit further includes instructions for carrying out the methods described herein.

BRIEF DESCRIPTION OF THE DRAWINGS

FIG. 2 is a schematic cross-sectional side view of a lateral flow device according to an embodiment. In this embodiment, the lowest point of each reservoir is below the plane of the planar region of the wicking pad onto which the substrate is placed. The cross-sectional shape of each reservoir is a "V".

FIG. 3 is a schematic cross-sectional side view of a lateral flow device according to an embodiment in which the lowest point of each reservoir is above the plane of the planar region of the wicking pad onto which the substrate is placed. The cross-sectional shape of each reservoir is a "V".

FIG. 5A shows a substrate and a pump in intimate contact with the wicking pad. The wicking pad is substantially entirely bonded to the plastic molded base which is the base of the device.

FIG. 6A shows a substrate and a pump in intimate contact with the wicking pad. The wicking pad is substantially entirely bonded to the plastic molded base which is the base of the device.

In FIGS. 7 and 8, a lowest point of each reservoir is below the planar region of the wicking pad onto which the substrate is placed. In FIGS. 9 and 10, a lowest point of each reservoir is on the same plane as the planar region of the wicking pad onto which the substrate is placed. In FIGS. 7 and 9, the reservoirs are attached to each other on at least one side. In FIGS. 8 and 10, the reservoirs are not attached to each other on at least one side. The devices in FIGS. 7-10 are shown without a pump.

FIGS. 12-14 are schematic cross-sectional side views of lateral flow devices according to embodiments in which the wicking pad is at least partially bonded to a cover. Portions of the wicking pad are formed (e.g., folded) into protrusions that project into the reservoirs (shown with reagent solution therein) when the cover is placed onto the device. In FIG. 12, sections of the wicking pad between the protrusions are bonded to the cover. In FIGS. 13 and 14, sections of the wicking pad between the protrusions are bonded to the base at edges between the reservoirs.

FIGS. 18A-18C are immunoblotting results using the lateral flow device of FIGS. 4A and 4B and as described in Example 2.

DETAILED DESCRIPTION

Figure 1:
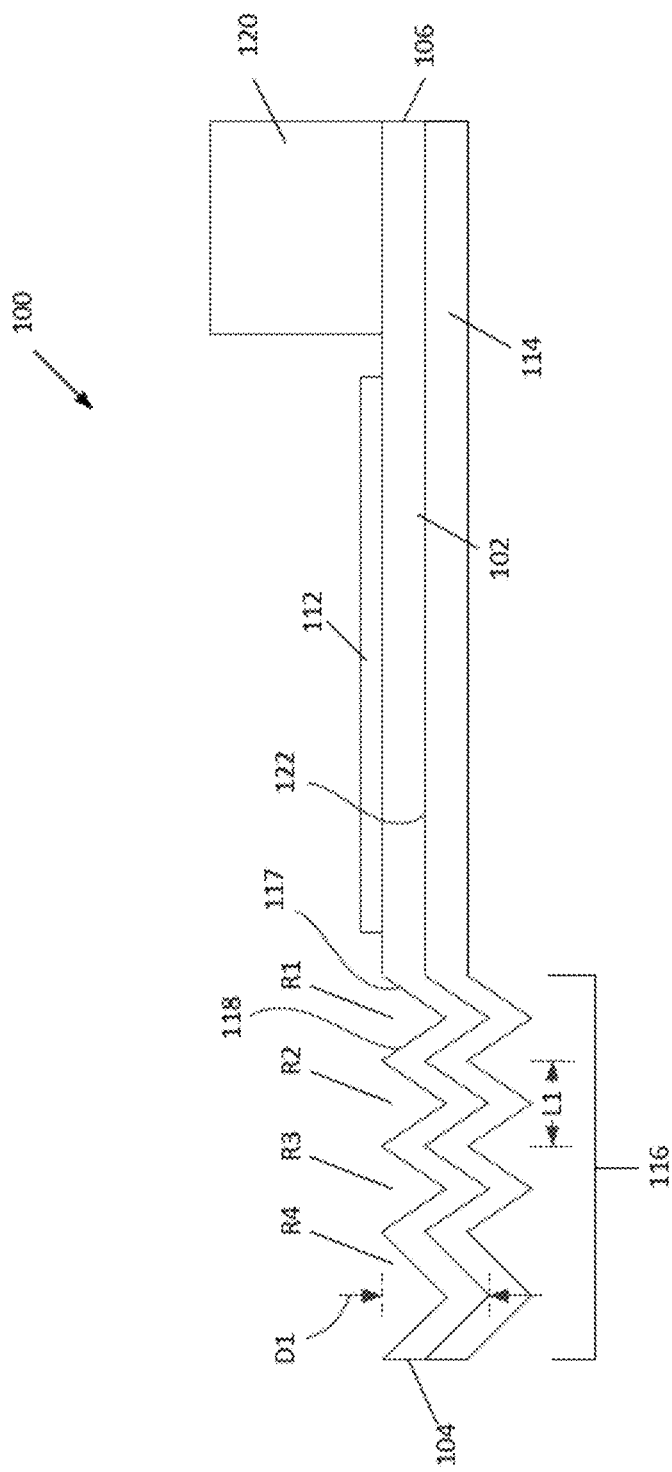
FIG. 1 is a schematic cross-sectional side view of a lateral flow device according to an embodiment. The device includes a base having four reservoirs that sequentially deliver reagent solutions to a wicking pad in intimate contact with the base. The wicking pad follows the contours of the reservoirs. The lowest point of each reservoir is below the plane of the planar region of the wicking pad onto which a substrate is placed. The cross-sectional shape of each reservoir is a "V". The device is shown with the substrate in intimate contact with the wicking pad.

Described herein are lateral flow devices and methods of using such devices that allow for efficient lateral flow detection of analytes (e.g., proteins, nucleic acids) immobilized on substrates (e.g., western blot membranes) or the wicking pad (e.g., a diagnostic application) using specific binding agents (e.g., antibodies). The devices and methods described herein also allow for efficient lateral flow detection of analytes captured by specific binding agents immobilized on substrates. Lateral flow devices and methods of using such devices have been discovered that deliver different solutions (e.g., samples having one or more analytes, specific binding agents, running buffer, wash solutions) sequentially and hands-free to a wicking pad in intimate contact with a substrate having analytes or binding agents immobilized thereon. The solutions are delivered sequentially to the wicking pad from at least two reservoirs molded into the base of the lateral flow devices. In some embodiments, the devices described herein can be configured in a single-use device, allowing for an affordable and simple assay format.

I. Definitions

The term "analyte" refers to a biological molecule, e.g., a protein, nucleic acid, polysaccharide, lipid, antigen, growth factor, hapten, etc., or a portion thereof. Analytes can be reversibly or irreversibly immobilized on a surface, such as a membrane or a wicking pad and detected as described herein.

The term "immobilized" or "embedded" interchangeably refers to reversibly or irreversibly immobilized molecules (e.g., analytes or binding agents). In some embodiments, reversibly immobilized molecules are immobilized in a manner that allows the molecules, or a portion thereof (e.g., at least 25%, 50%, 60%, 75%, 80% or more of the molecules), to be removed from their immobilized location without substantial denaturation or aggregation. For example, a molecule can be reversibly immobilized in or on an absorbent material (e.g., an absorbent pad) by contacting a solution containing the molecule with the absorbent material, thereby soaking up the solution and reversibly immobilizing the molecule. The reversibly immobilized molecule can then be removed by wicking the solution from the absorbent material, or from one region of the absorbent material to another. In some cases, a molecule can be reversibly immobilized on an absorbent material by contacting a solution containing the molecule with the absorbent material, thereby soaking up the solution, and then drying the solution-containing absorbent material. The reversibly immobilized molecule can then be removed by contacting the absorbent material with another solution of the same or a different composition, thereby solubilizing the reversibly immobilized molecule, and then wicking the solution from the absorbent material, or from one region of the absorbent material to another.

Irreversibly immobilized molecules (e.g., binding agents or analytes) are immobilized such that they are not removed, or not substantially removed, from their location under mild conditions (e.g., pH between about 4-9, temperature of between about 4-65° C.). Exemplary irreversibly immobilized molecules include protein analytes or binding agents bound to a nitrocellulose, polyvinylidene fluoride, nylon or polysulfone membrane by standard blotting techniques (e.g., electroblotting). Other exemplary irreversibly immobilized molecules include protein analytes or binding agents bound to glass or plastic (e.g., a microarray, a microfluidic chip, a glass histology slide or a plastic microtiter plate having wells with bound protein analytes therein).

The term "binding agent" refers to a agent that specifically binds to a molecule such as an analyte. While antibodies are described in many contexts herein, it will be understood that other binding agents can be used instead of antibodies as preferred by the user. A wide variety of binding agents are known in the art, including antibodies, aptamers, affimers, lipocalins (e.g., anticalins), thioredoxin A, bilin binding protein, or proteins containing an ankyrin repeat, the Z domain of staphylococcal protein A, or a fibronectin type III domain. Other binding agents include, but are not limited to, biotin/streptavidin, chelating agents, chromatography resins, affinity tags, or functionalized beads, nanoparticles and magnetic particles.

The term "specifically bind" refers to a molecule (e.g., binding agent such as an antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, 100-fold, or 1000-fold or more greater affinity.

The term "antibody" refers to a polypeptide comprising a framework region from an immunoglobulin gene, or fragments thereof, that specifically bind and recognize an antigen, e.g., a particular analyte. Typically, the "variable region" contains the antigen-binding region of the antibody (or its functional equivalent) and is most critical in specificity and affinity of binding. See Paul, *Fundamental Immunology* (2003). Antibodies include for example chimeric, human, humanized antibodies, or single-chain antibodies.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

As used in this specification and the appended claims, the singular forms "a", "an", and "the" include plural referents unless the content clearly dictates otherwise. As used herein, the term "about" refers to the recited number and any value within 10% of the recited number. Thus, "about 5" refers to any value between 4.5 and 5.5, including 4.5 and 5.5.

II. Devices

FIGS. 1-15 illustrate embodiments of lateral flow devices for detecting analytes on a substrate, for detecting analytes bound to binding agents on a substrate, or for detecting analytes bound to binding agents on a wicking pad.

Figure 4A:
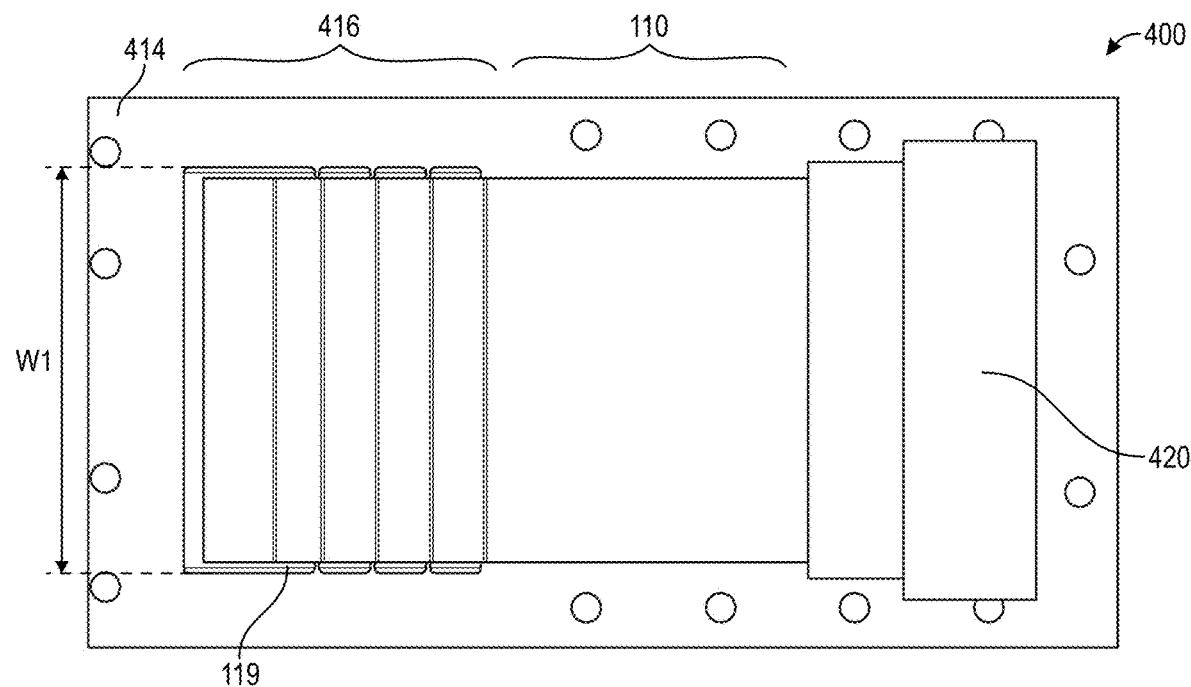
FIGS. 4A and 4B are top and side perspective views, respectively, of a lateral flow device according to an embodiment in which the lowest point of each reservoir is below the planar region of the wicking pad onto which the substrate is placed. The cross-sectional shape of each reservoir is a "V". In this embodiment, the wicking pad is substantially entirely bonded to the plastic molded base which is the base of the device.
Figure 4B:
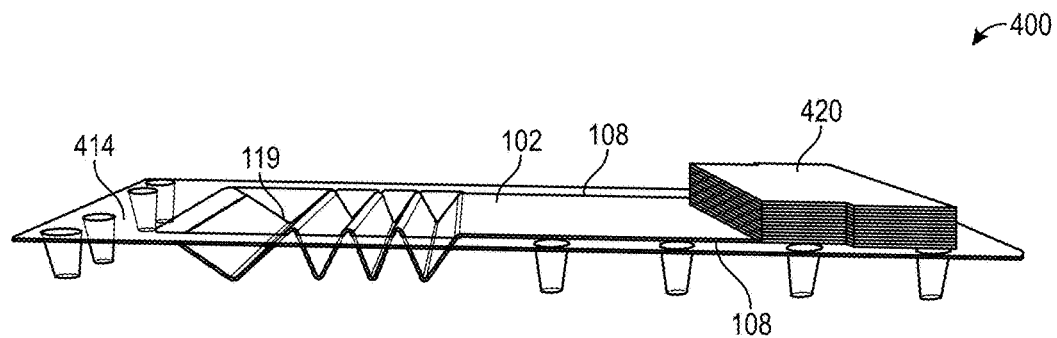
Figure 5A:
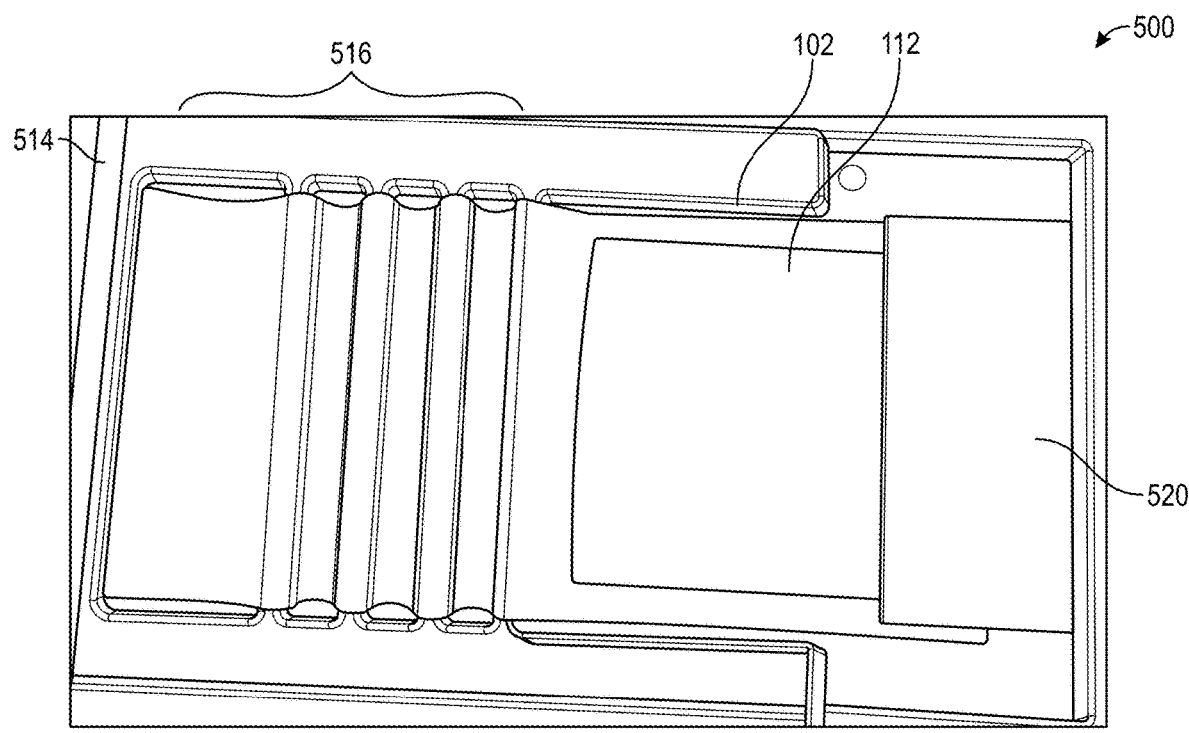
FIGS. 5A and 5B are top and side perspective views, respectively, of a lateral flow device according to an embodiment in which the cross-sectional shape of each reservoir is a semi-circle. In this embodiment, a lowest point of each reservoir is on the same plane as the planar region of the wicking pad onto which the substrate is placed.
Figure 5B:
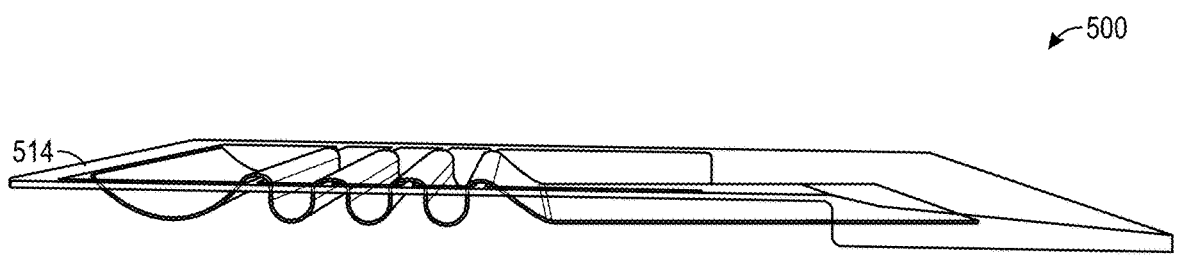
Figure 6A:
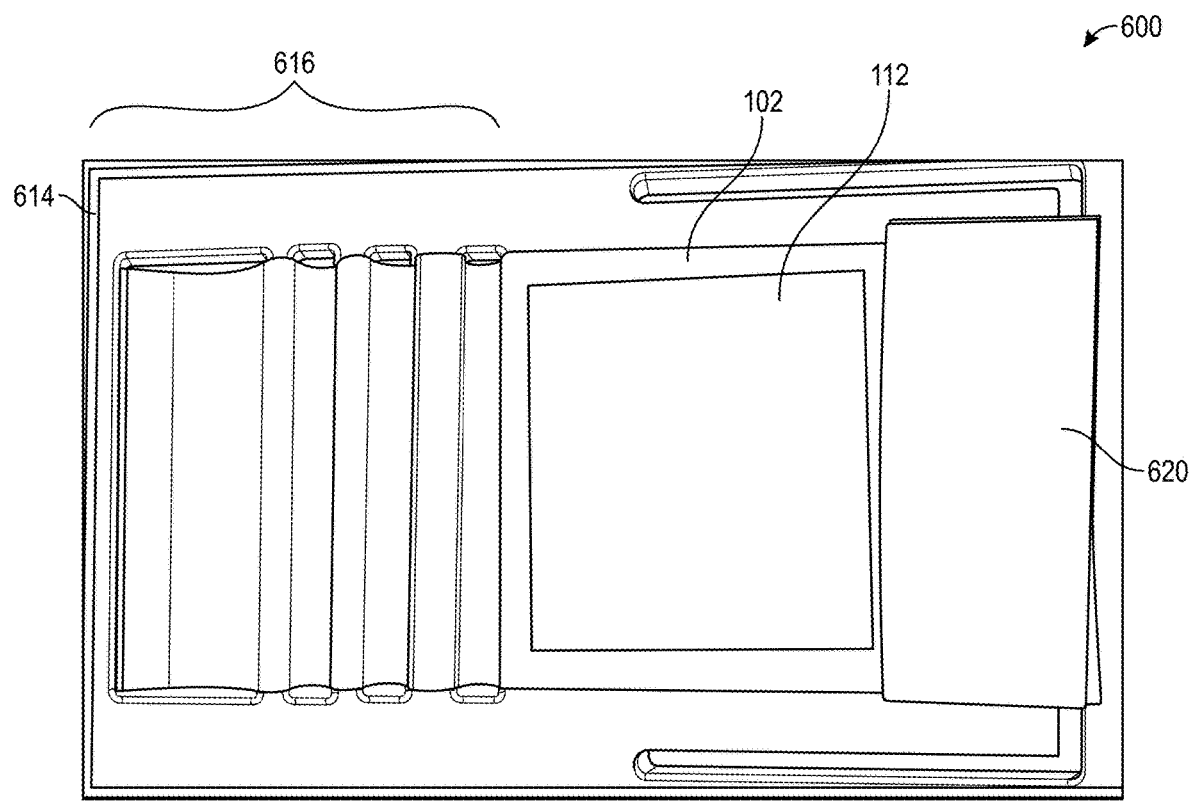
FIGS. 6A and 6B are top and side perspective views, respectively, of a lateral flow device according to an embodiment in which the cross-sectional shape of each reservoir is a semi-circle. In this embodiment, a lowest point of each reservoir is below the plane of the planar region of the wicking pad onto which the substrate is placed.
Figure 6B:
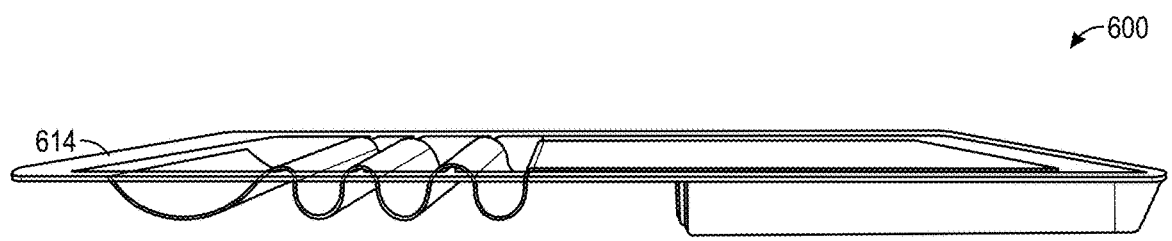
Figure 7:
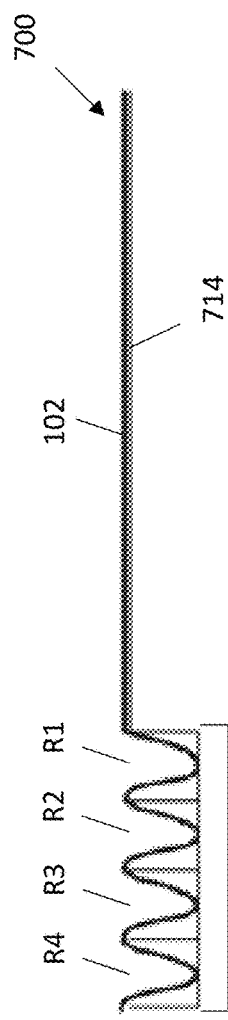
FIGS. 7-10 are schematic side views of lateral flow devices according to embodiments. In each embodiment, the cross-sectional shape of each reservoir is a square. The wicking pad is partially in intimate contact with the base (i.e., the wicking pad does not follow the contours of the reservoirs).

Referring to FIGS. 1 and 4A-4B, a lateral flow device 100 includes a wicking pad 102 having a first end 104, a second end 106, two lateral edges 108, and a planar region 110 for contacting a substrate 112 (e.g., a membrane) comprising immobilized analytes or proteins (e.g., a western blot, a dot blot) to be detected. The lateral flow device 100 also includes a base 114 comprising two or more reservoirs 116 (e.g, depressions or troughs) spatially separated from each other. In some embodiments, each reservoir has a longest dimension perpendicular to the lateral edges 108 of the wicking pad 102. Each reservoir is therefore oriented perpendicular to the direction of lateral flow. In certain embodiments, one or more reservoirs have a longer dimension parallel to the lateral edges of the wicking pad 102. The reservoirs 116 (e.g., R1, R2, R3, and R4) are located at or near the first end 104 of the wicking pad 102. Each of the reservoirs 116 receives and is in fluid communication with the first end 104 of the wicking pad 102 (i.e., liquid, when present in the reservoirs 116, can flow from each of the reservoirs 116 into the wicking pad 102). The reservoirs 116 supply liquid (e.g., buffers and detection reagents) sequentially to the wicking pad 102 and into the planar region 110 for applying the substrate 112. The planar region 110 is located downstream from the reservoirs 116 and upstream from a pump 120 (e.g., between the reservoirs 116 and the pump 120). The pump 120 is located on or adjacent to the second end 106 of and in intimate contact with the wicking pad 102. The dry pump 120 acts as a drain by wicking the liquid from the reservoirs 116 through the wicking pad 102.

Figure 8:
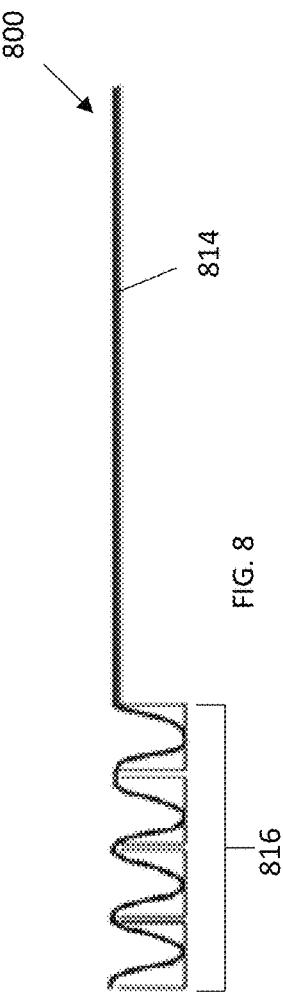
Figure 9:
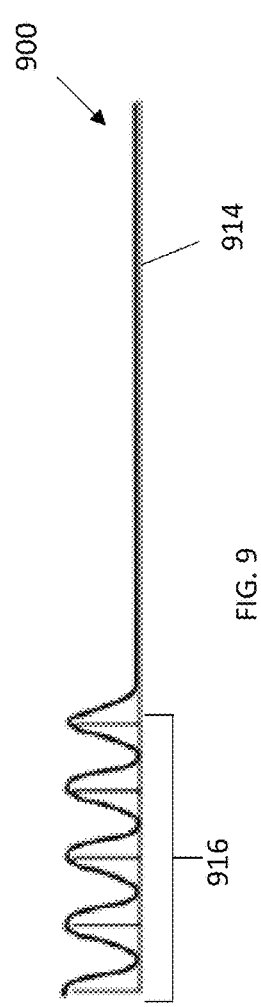
Figure 10:
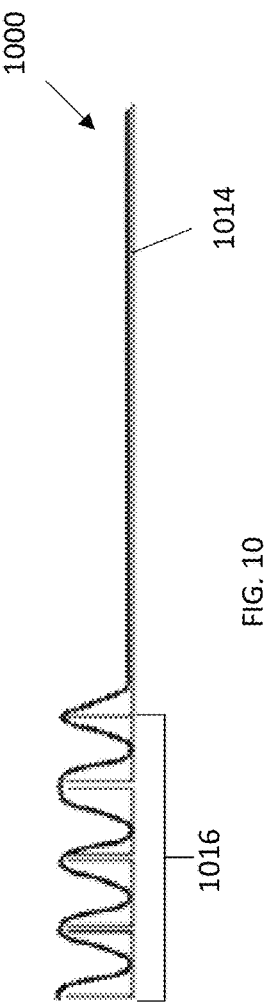

Each of the reservoirs is bounded by a first wall 117 and a second wall 118 oriented perpendicular to the flow of liquid. Each of the reservoirs is further bounded by two end walls 119. In some embodiments, an edge of the second wall 118 of a first reservoir R1 is attached to an edge of the first wall 117 of a second reservoir R2. In certain embodiments, the reservoirs share a wall. For example, the second wall of the first reservoir R1 can be the first wall of the second reservoir R2 (e.g., FIGS. 7 and 9). In some embodiments, the reservoirs are not attached to each other, nor do the reservoirs share a wall (FIGS. 8 and 10).

In some embodiments, each of the reservoirs 116 spans the width of the wicking pad 102. In some embodiments, a lowest point of one or more of the reservoirs is located substantially below the plane of the planar region 110 of the wicking pad 102 (see FIGS. 1-2, 4A-4B, 6A-6B, 7-8, 11-15). In certain embodiments, the lowest point of one or more of the reservoirs 116 is located substantially in the plane of the planar region 110 (see FIGS. 5A-5B, 9-10). In some embodiments, the lowest point of one or more of the reservoirs 116 is located substantially above the plane of the planar region 110 (see FIG. 3). In certain embodiments, the lowest point of all of the reservoirs 116 is located on the same plane which can be on, above or below the plane of the planar region 110.

Referring again to FIGS. 1 and 4A-4B, the reservoirs 116 can be any size and shape. In some embodiments, each of the reservoirs 116 comprises a length L1, a width W1, and a depth D1. In some embodiments, each of the reservoirs is at least about 0.1, 0.5, 1.0, 8.5, 13.5, 20 cm or more in at least one dimension. In some cases, the length L1 and the width W1 of each of the reservoirs 116 are at least about 2-fold, 3-fold, 5-fold, 10-fold, 100-fold or more larger than the depth D1. In some embodiments, each of the reservoirs is sized to match the width of the wicking pad 102 and has a width W1 that is at least about 3-fold, 4-fold, 5-fold, 6-fold, 8-fold, 10-fold, 13-fold, 17-fold, 20-fold, 27-fold or more larger than the length L1. Exemplary sizes of each reservoir include, but are not limited to, about 0.5 cm×8.5 cm, 1×3 cm, 3 cm×3 cm, 2.5 cm×about 8.5 cm, 1 cm×10 cm, 3 cm×10 cm, 2 cm×13.5 cm, 3×13.5 cm, 1 cm×15 cm, 3 cm×15 cm, or 3.5 cm×20 cm in length L1 and width W1, respectively. As shown in FIGS. 1-17E, the "length L1" is based on the direction of flow and is the shortest dimension. In some embodiments, each reservoir is 3 cm in length L1 by 10 cm in width W1. In some cases, each reagent reservoir is 1±0.5, 1, 2 or 3 cm in length L1 by 10±0.5 cm or 15±0.5 cm in width W1. In some cases, the length L1 is the longer dimension and one or more of the reservoirs is about 1 cm to about 5 cm in length L1 by about 0.5 cm to about 5 cm in width W1. In some cases, the depth D1 of at least one reservoir is about 0.5 cm, about 1 cm, about 2 cm, or about 3 cm.

In certain embodiments, a cross-section of each of the reservoirs 116 has a "V shape (FIGS. 1-3, 4A-4B), a semicircle shape (FIGS. 5A-6B), an oval shape, a "U" shape, a rectangle shape, a square shape (FIGS. 7-10), or a trapezoid shape (FIGS. 11-15). In some embodiments, the first wall 117 and the second wall 118 of each of the reservoirs 116 has a slope ranging from about 30 degrees to about 90 degrees relative to a horizontal plane. In certain embodiments, the end walls 119 of each of the reservoirs 116 have a slope of about 90 degrees relative to a horizontal plane. The depth D1 of the reservoirs 116 and the slope of the first and second walls can be chosen to control the overall flow rate of reagent solutions exiting the reservoirs 116, with deeper depressions or steeper walls slowing the lateral flow rate and more shallow sloped walls resulting in faster flow rates. The volume of each of the reservoirs 116 is determined by many factors including, but not limited to, the size and shape of the reservoirs 116 and the configuration of the lateral flow device 100. In some embodiments, each reservoir has a capacity of at least about 0.1 milliliters to about 30 milliliters.

As shown in FIGS. 4A-6B, the reservoirs 116 comprise one set of four reservoirs. In some embodiments (FIG. 16), the reservoirs comprise two or more sets 1640 of reservoirs spatially separated from each other (e.g., separated by a wall or a distance) such that multiple substrates can be analyzed at one time. In some embodiments, the sets 1640 of reservoirs are adjacent to each other on the width axis of the lateral flow device 1640. The sets 1640 of reservoirs are arranged to run in parallel to each other in a side-by-side relationship. Each set of reservoirs is functionally independent of the adjacent set of reservoirs.

Figure 16:
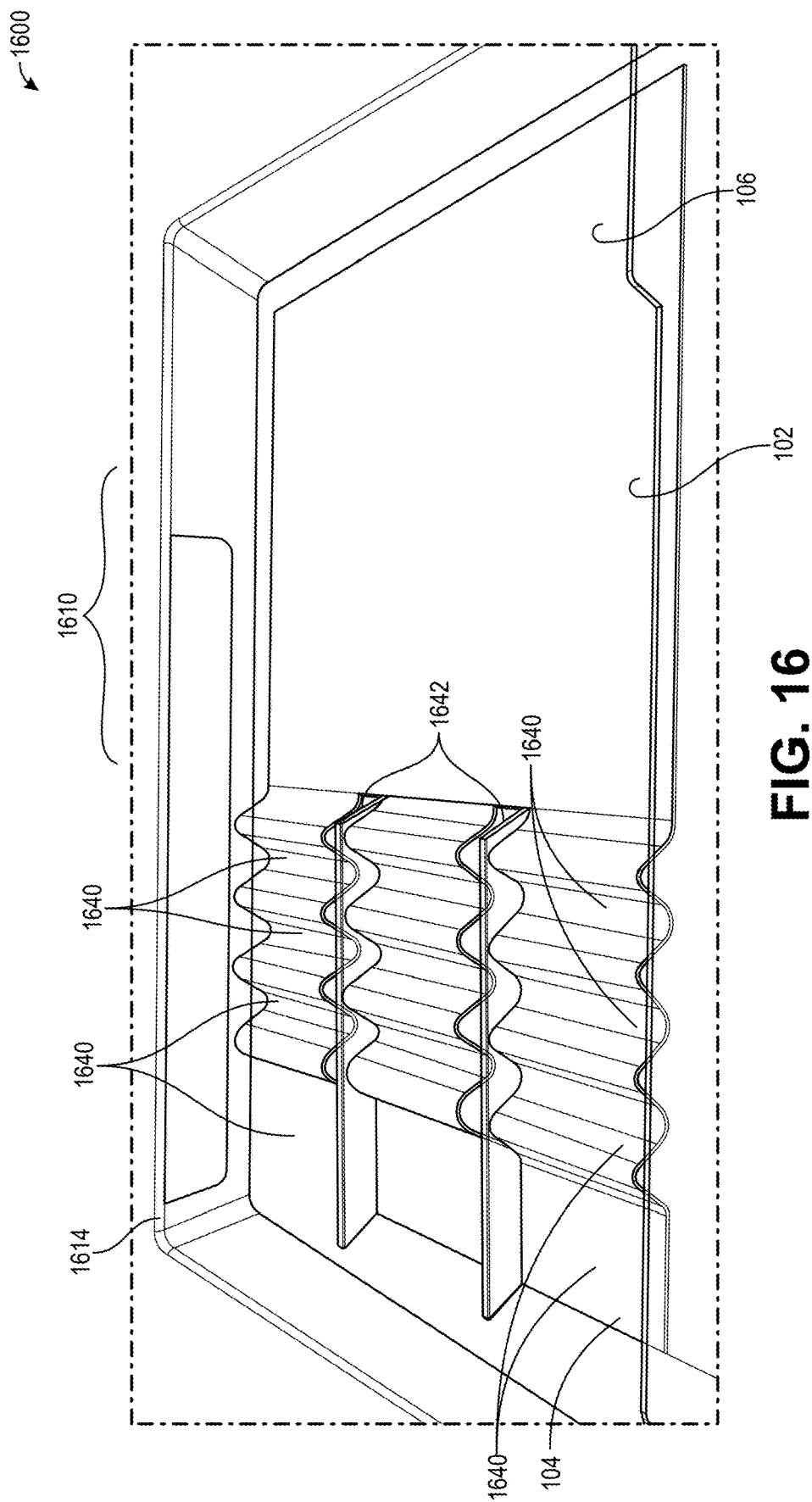
FIG. 16 is a perspective view of a lateral flow device according to an embodiment comprising a plurality of sets of reservoirs. The device can be used to analyze multiple substrates simultaneously. The device is shown with no substrate or pump.

In embodiments having sets of reservoirs, one or more dividing walls 1642 between the sets of reservoirs can be molded into the base 1614 of the lateral flow device 1600 as shown in FIG. 16. In some embodiments, the dividing walls 1642 are formed by inserting/attaching a barrier to the base 1614 using adhesive, silicone, or caulking. In some embodiments, the dividing walls 1642 are formed by inserting one or more walls into compatible slots in the base 1614. Barriers may be formed from wax or acrylic that is printed or deposited in one or more layers to create a desired barrier height. The barrier can also be made of a hydrophobic or impermeable material (e.g., wax, acrylic, silicone) to prevent flow of aqueous solutions between the sets of reservoirs. In some embodiments, the barrier extends from the first end 104 of the wicking pad 102 to the planar region 1610 for applying the substrate. In certain embodiments, the barrier(s) extend from the reservoirs to the end of the planar region 1610 to inhibit, eliminate, or substantially eliminate fluid communication (e.g., fluid flow) between adjacent zones in the wicking pad and allow for simultaneous processing of multiple substrates. In some embodiments, the barrier extends from the first end 104 to the second end 106 of the wicking pad 102 (i.e., substantially the entire length of the wicking pad). In an embodiment in which the barrier does not extend to the second end 106 of the wicking pad 102, a single pump can extend across the width of the second end of the wicking pad and can be used to process multiple substrates. In embodiments in which the barriers extend from the first end to the second end of the wicking pad, each zone of the wicking pad can have a separate pump. In some embodiments, barriers can be a mix of different formats. For example, the reservoir sets can be separated via a molded dividing wall and zones downstream from the reservoirs can be separated by a wax barrier or a region in which the wicking pad has been removed from the base to form a gap between the zones. When the lateral flow device is in use, the barriers or gaps in the wicking pad help to control the fluid flow in a linear direction to the pump.

Hydrophobic barriers include, but are not limited to, wax barriers, or barriers created by vapor or liquid phase silanization of the wicking pad. Exemplary materials from which impermeable barriers can be formed include, but are not limited to, wax, plastic, polymers, and resin.

The wax used to form the wax barriers can be any wax that is flowable at elevated temperatures and non-flowable at ambient temperature (e.g., about 20-25° C.). Examples are paraffin waxes, microcrystalline waxes, thermoset waxes, animal waxes such as beeswax, lanolin, and tallow, vegetable waxes such as soy, carnauba, candelilla and palm waxes, mineral waxes such as ceresin and montan waxes, petroleum waxes, and synthetic waxes such as ethylenic polymers, chlorinated naphthalenes, and Fischer-Tropsch waxes. Paraffin wax compositions may contain, in addition to n-paraffins and isoparaffins, minor amounts of cyclo-paraffins or olefins, or both. Waxes that become flowable, i.e., that have melting points, within the temperature range of from about 60° C. to about 150° C., or from about 75° C. to about 125° C., are among those that can be used. Wax formulations and compositions that behave in this manner are known to those of skill in the art.

The silanization reagent used to form hydrophobic barriers can be any silanization reagent that reacts with the wicking pad, or a portion thereof. For example, if the wicking pad contains cellulose, a silanization reagent that silanizes hydroxyl groups of the cellulose backbone can be utilized. Exemplary silanization reagents include, but are not limited to, trimethylchlorosilane, trimethylsilane, or hexamethyldisilazane. Silanization reagents further include triethoxysilanes (R—Si(C2HSO)3) where R is, for example, vinyl, methacrylol, aminopropyl, fluoroalkyl, or thioethyl. Other suitable silanization reagents will be readily apparent to those of skill in the art. Polymers can be reacted with the silane groups to create an impermeable barrier.

The wax or other barrier forming reagent (e.g., silanization reagent, or impermeable barrier) can be applied to one side or both sides of the wicking pad, although in most cases, application to one side will be sufficient, provided that the wax or reagent penetrates, or is made to penetrate (e.g., by melting after application), the wicking pad to a degree sufficient to serve as a barrier to the flow of liquid. The barrier forming reagent can be applied as a liquid. The liquid can be applied by hand or other apparatus. In some cases, the liquid is sprayed or poured onto the wicking pad. Spraying can be accomplished with an inkjet printer or similar apparatus. In some cases, the liquid hardens after application to form an impermeable and/or hydrophobic barrier. Alternatively, the barrier forming reagent can be applied as a vapor. For example, a silanization reagent, wax, plastic, resin, or polymer can be applied as a vapor that condenses on the wicking pad or reacts with the wicking pad. Alternatively, the barrier forming reagent can be applied as a solid. For example, wax can be applied as a solid manually or in an automated or mechanized fashion. In some cases, the wicking pad is masked to protect regions from the barrier forming reagent, and the barrier forming reagent is contacted with the wicking pad.

Application of wax can be achieved by hand, either by the use of a common crayon or by a wax pen, or by a wax printer. Wax pens are known in the art and commonly include a housing having a reservoir to contain hot wax, a spout, and a handle. Application of the hot wax is achieved by tipping the housing to cause the liquefied wax to pass through the spout, and the housing is equipped with a valve to stop the flow of the wax at the terminus of a printed line.

Wax printers are likewise known in the art and commonly operated by thermal transfer printing using a print head that includes an array of very small heating elements that are software-controlled for independent activation to produce localized heating of the wax above its melting point to release the wax to the print medium. Commercially available examples of wax printers include the Phaser 8560DN (Fuji Xerox, Ltd., Japan), and the CALCOMP COLORMASTER PLUS thermal wax transfer printer (CalComp Graphics, LLC, Foothill Ranch, Calif., USA).

In some embodiments, once applied, the wax can be made to penetrate the bulk thickness of the wicking pad to fill the pores and form a lateral barrier to aqueous fluid flow by heating the wax above its melting point. In some cases, the amount of wax applied will be such that full penetration of the thickness of the wicking pad with the melted wax will occur while lateral flow of the melted wax (i.e., in directions parallel to the lateral edges of the wicking pad) is minimal or at least limited to a small distance that is substantially uniform along the length of a line of applied wax so that the resulting area bordered by the wax barrier is known and controlled. The formation of the barrier in this manner can also be controlled by the degree of heating, including the temperature to which the wax is heated and the length of time that the heating is continued. Optimal temperatures and durations are readily determinable by routine trial and error, but in most cases serviceable results will be obtained by heating to at least 5° C. above the wax melting point, and in many cases from about 5 to about 50° C. above the melting point, or from about 10 to about 30° C. above the melting point. The most appropriate heating time will depend on the temperature, higher temperatures requiring less time. In general, heating times ranging from about fifteen seconds to about twenty minutes, or in many cases from about thirty seconds to about ten minutes, will provide useful results. Heating can be achieved by conventional means, including radiative heating, conductive heating, convective heating, impulse heating, and microwave heating. Effective results can be achieved with equipment as simple as a hot plate or a conventional oven.

The width of each of the reservoirs in the sets will depend on the required number of sets of reservoirs and the width of the wicking pad. In some embodiments having multiple sets of reservoirs, the width of the reservoir is about 3 mm to about 3 cm. Likewise, the dividing walls or barriers can be any thickness as long as they prevent cross communication of reagents placed into adjacent reservoirs. Optimal widths for hydrophobic or impermeable barriers may vary with the dimensions of the area to be bordered by the barrier and with the thickness of the wicking pad and are readily determinable by routine testing. In most cases, the width will range from about 10 microns to about 5 mm, from about thirty microns to about 3 mm, from about 100 microns to about 1 mm, or from about 200 microns to about 5 mm, or 10 mm.

In certain embodiments, the wicking pad 102 is substantially entirely in intimate contact with an upper surface of the base and follows the contours of the base (FIGS. 1-6B). In some embodiments, the wicking pad 102 is not bonded to the end walls 119 of the reservoirs. In certain embodiments, the wicking pad 102 is substantially entirely bonded to an upper surface of the base (FIGS. 1-6B). In some embodiments, a part of the wicking pad 102 (e.g., the portion in fluid communication with each of the reservoirs 116) is in intimate contact with or is bonded to the upper surface 122 of the base 114 and follows the contours of the first and second walls 117, 118 of each of the reservoirs 116. In certain embodiments, only the planar region 110 and the second end 106 are bonded to the upper surface of the base (FIGS. 7-10). Bonding the wicking pad 102 to the upper surface of the base can prevent fluid flow on the underside of the wicking pad 102.

Lateral flow devices having a cover that covers or attaches to the base are illustrated in FIGS. 11-15. Each of the lateral flow devices 1100, 1200, 1300, 1400, 1500 includes a wicking pad 102 having a first end 104, a second end 106, two lateral edges 108, and a planar region 110 for contacting a substrate 112 comprising immobilized analytes or proteins to be detected. Each of the lateral flow devices 1100, 1200, 1300, 1400, 1500 also include a base 1114, 1214, 1314, 1414, 1514 comprising two or more reservoirs 1116, 1216, 1316, 1416, 1516 (e.g, depressions or troughs) spatially separated from each other. Each reservoir has a longest dimension perpendicular to the lateral edges of the wicking pad. The reservoirs 1116, 1216, 1316, 1416, 1516 are located at or near the first end 104 of the wicking pad 102. Each of the reservoirs 1116, 1216, 1316, 1416, 1516 receives and is in fluid communication with the first end 104 of the wicking pad 102 (i.e., liquid, when present in the reservoirs 1116, 1216, 1316, 1416, 1516 can flow from each of the reservoirs 1116, 1216, 1316, 1416, 1516 to the wicking pad 102). The reservoirs 1116, 1216, 1316, 1416, 1516 supply liquid (e.g., buffers and detection reagents) sequentially to the wicking pad 102 and into the planar region 110 for applying the substrate 112. Each of the reservoirs is bounded by a first wall 1117, 1217, 1317, 1417, 1517 and a second wall 1118, 1218, 1318, 1418, 1518 oriented perpendicular to the flow of liquid. Each of the reservoirs is further bounded by two end walls. In some embodiments, an edge of the second wall 1118, 1218, 1318, 1418, 1518 of a first reservoir R1 is attached to an edge of the first wall of a second reservoir R2.

Figure 11:
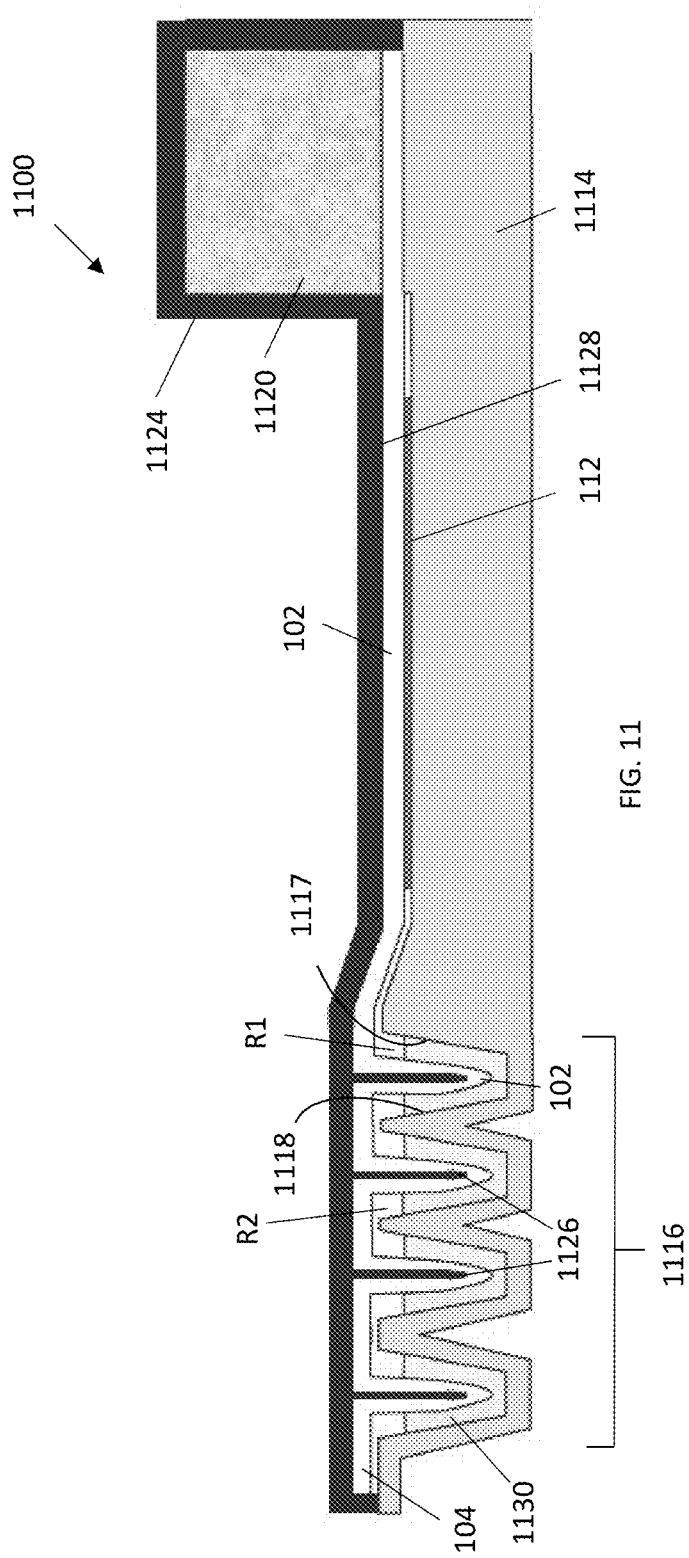
FIG. 11 is a schematic cross-sectional side view of a lateral flow device according to an embodiment in which the wicking pad is at least partially bonded to a cover. The wicking pad follows the contours and is bonded to projections that project into the reservoirs (shown with reagent solution therein) when the cover is placed onto the device.

In some embodiments, the lateral flow device 1100 includes a cover 1124 having two or more projections 1126 each of which projects into a different reservoir (FIG. 11). The projections 1126 can be sized to project partially or completely into the reservoirs when the cover 1124 is placed onto the device 1100. For example, a tip of each of the projections 1126 can be in close proximity to the bottom of the reservoirs when the cover is placed on the device. In some embodiments, each of the projections 1126 is a blade spanning the width of the reservoir into which the blade projects.

In certain embodiments having a cover, the wicking pad 102 is in intimate contact with all or part of a lower surface 1128, 1228, 1328, 1428 of the cover 1124, 1224, 1324, 1424 (FIGS. 11-14). For example, as illustrated in FIG. 11, the wicking pad can follow the contours of the cover 1120 including the projections 1126 such that the wicking pad contacts reagent solution 1130 in the reservoirs when the cover 1124 is placed on the device 1100. In some embodiments, all or a part of the wicking pad 102 is bonded to the cover. For example, the wicking pad 102 can be bonded to all or part of the projections 1126 in the cover 1124. In certain embodiments, the wicking pad 102 is not bonded to the cover and the projections urge the wicking pad into the reservoirs when the cover is placed on the device 1100. In some embodiments, the wicking pad 102 is bonded only to the cover in the planar region 110 that contacts the substrate 112 (FIGS. 12-14).

Figure 15:
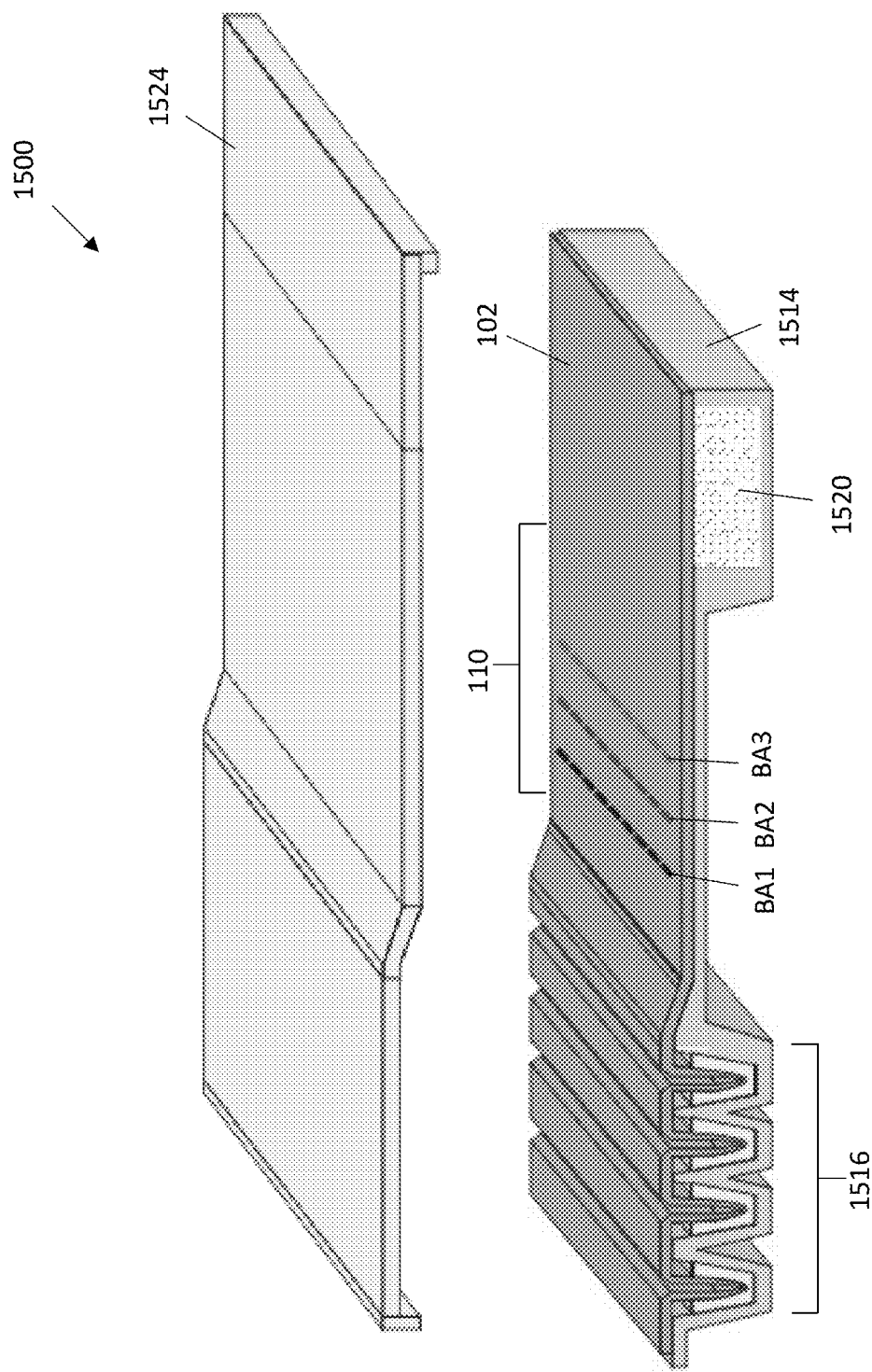
FIG. 15 is a schematic perspective view of a lateral flow device according to an embodiment in which binding agents are immobilized on a planar region of the wicking pad downstream from the reservoirs.

As shown in FIGS. 11-14, a lower surface of the wicking pad contacts the substrate 112. In an embodiment in which the wicking pad 102 is not bonded nor is in intimate contact with the cover, the substrate 112 can contact an upper or lower surface of the wicking pad 102. As illustrated in FIG. 15, in an embodiment not having a substrate and in which binding agents (e.g., BA1, BA2, and BA3) are immobilized (e.g. are printed in lines or spots) on or in planar region 110 of the wicking pad 102 (e.g. an embodiment used in a diagnostic assay), a lower surface of the planar region 110 is in intimate contact or is bonded to the base.

As illustrated in FIGS. 12-15, portions of the wicking pad 102 near the first end 104 can be folded such that protrusions 105 are formed in the wicking pad 102. The protrusions 105 dip into the reservoirs when the cover is placed onto the device. When the cover is placed onto the device, the protrusions 105 contact the reagent solutions, when present, in the reservoirs. Sections of the wicking pad 102 between the protrusions 105 can contact or be bonded to the cover (FIG. 11) or the base (FIGS. 12-14).

The lateral flow devices 1100, 1200, 1300, 1400, 1500 further include a pump 1120, 1220, 1320, 1420, 1520 located on or adjacent to the second end 106 of and in intimate contact with the wicking pad 102. The pump 1120, 1220, 1320, 1420, 1520 can contact an upper surface (FIGS. 11-13) or a lower surface (FIGS. 14 and 15) of the second end 106 of the wicking pad 102. The pump 1120, 1220, 1320, 1420, 1520 can further be substantially entirely contained in the cover or the base of the device.

The planar region 110 of the wicking pad 102 can include drawings/markings or other indications for where a user should place the substrate 112 or where binding agents are immobilized in/on the wicking pad. Alternately, the drawing/markings can be on the device cover or base.

The wicking pad 102 has a width, a length, and a height (e.g., a thickness). The wicking pad 102 can be any size and shape. In certain embodiments, at least a section (e.g., the planar region 110 for applying the substrate 112) of the wicking pad 102 is planar. In some cases, the length and the width of the wicking pad 102 are at least about 2-fold, 5-fold, 10-fold, 100-fold or more larger than the height (i.e., thickness).

Exemplary sizes for wicking pads include, without limitation, wicking pads that are at least about 0.25 cm, 0.5 cm, 1 cm, 2 cm, 3 cm, 4 cm, 5 cm, 6 cm, 7 cm, 8 cm, 10 cm, 12 cm, 15 cm, 20 cm, 25 cm, 30 cm or more in at least one dimension. In some cases, the wicking pad 102 is 20±0.5, 1, 2, 3, 4, 5, 6, 9 or 10 cm in length by 10±0.5, 1, 2, 3, 4, 5, 6, 7, 8, or 9 cm in width.

The wicking pad 102 is an absorbent material. In some embodiments, the wicking pad 102 is configured to have a high solution capacity and a lateral flow rate. In some cases, the high solution capacity and lateral flow rate are provided by having a wicking pad 102 with substantial height (e.g., thickness). In some cases, the wicking pad 102 is about 10, 9, 8, 7, 6, 5, 4, 3, 2, 1, 0.75, 0.5, or about 0.2 mm thick. In some cases, the wicking pad 102 is between about 0.05 mm and about 0.5 mm thick.

In some embodiments, the wicking pad 102 has one or more reagents (e.g., binding agents BA1, BA2, BA3 in FIG. 15) immobilized or embedded therein in one or more zones (e.g., in one or more zones downstream from the reservoirs 116 or in a zone inside each of the reservoirs 116). The embedded reagents are generally embedded or bound and dried into the wicking pad such that the reagents remain immobile during fluid flow or such that the reagent are immobile until contacted by an aqueous fluid front under lateral flow and are released at a user-defined event. The zones can be printed lines or spots of reagent.

The wicking pad 102 generally has a large surface area due to the presence of a plurality of pores. The large surface area can increase the loading capacity of the wicking pad 102 for one or more reagents or one or more solutions containing a reagent. In some embodiments, the wicking pad 102 has a specific surface area of at least about 0.001 $m^2/g$, 0.02 $m^2/g$, 0.1 $m^2/g$, 0.5 $m^2/g$, 1 $m^2/g$, 10 $m^2/g$, or more as measured by standard techniques.

In some embodiments, the wicking pad 102 can have a particular pore size, a particular average pore size, or a particular pore size range. For example, the wicking pad 102 can contain 0.1 µm pores, 0.2 µm pores, 0.45 µm pores, or 1, 2, 4, 5, 6, 7, 8, 10, 15, 20 µm pores, or pores larger than about 20 µm. As another example, the wicking pad 102 can contain pores that average 0.1, 0.2, 0.45, 1, 2, 4, 5, 6, 7, 8, 10, 15, or 20 µm, or more in size. As another example, the wicking pad 102 can contain pores that range about 0.1-8 µm, 0.2-8 µm, 0.45-8 µm, 1-8 µm, 0.1-4 µm, 0.1-2 µm, 0.1-1 µm, 0.1-0.45 µm, 0.2-8 µm, 0.2-4 µm, 0.2-2 µm, 0.2-1 µm, 0.2-0.45 µm, 0.45-8 µm, 0.45-4 µm, 0.45-2 µm, 0.45-1 µm in size. In some cases, the wicking pad 102 can contain pores that are less than about 20 µm in size. For example, the wicking pad 102 can be composed of a material in which at least about 50%, 60%, 70%, 80%, 90% or more of the pores are less than about 20, 15, 10, or 5 µm in size. In some cases, the pores in the wicking pad 102 are large enough to contain one or more proteins of average size (e.g., about 1 nm). For example, the pores can be at least 1 nm in size, at least 5 nm in size, at least 10, 100, or 500 nm in size. Alternatively, at least 50%, 60%, 70%, 80%, 90% or more of the pores can be more than 1, 5, 10, 50, 100, or 500 nm in size. As used herein, pore size can be measured as a radius or a diameter. In some cases, the wicking pad 102 contains porous polyethylene, such as porous polyethylene having a pore size between 0.2 and 20 microns, or between 1 and 12 microns. The wicking pad 102 can have a different pore size in different regions of the pad. For example, the wicking pad 102 can have a lateral flow region that has a different pore size or pore size range. In some embodiments, pore size is chosen to control flow rate. For example, a larger pore size will allow for a faster flow rate.

The wicking pad 102 can be treated or functionalized to minimize non-specific reagent binding, increase lateral flow, increase wicking, or to reduce protein aggregation. For example, the wicking pad 102, or a portion thereof, can be treated to alter the hydrophilicity or alter the hydrophobicity of the treated area. In some cases, altering the hydrophilicity or hydrophobicity of the wicking pad 102 can increase binding agent loading, decrease binding agent aggregation or denaturation, create mask regions in which binding agent is excluded from or not loaded, or direct flow of binding agents when the wicking pad is wet. In some cases, the wicking pad contains a protein aggregation modifying agent as described herein.

The wicking pad 102, and the pump are generally formed of a bibulous material and can be made out of, for example, natural fibers, synthetic fibers, glass fibers or blends thereof. Non-limiting examples include cotton, glass, and combinations thereof. There are many commercial materials available for diagnostic uses from vendors including, but not limited to, Ahlstrom, GE, PALL, Millipore, Sartorius, and S&S.

The pump is formed from material having a liquid absorbing capacity that is significantly greater than the wicking pad 102. In some embodiments, the pump is formed from one or more absorbent pads.

The bibulous material can include, but is not limited to, polymer containing material. The polymer can be in the form of polymer beads, a polymer membrane, or a polymer monolith. In some cases, the polymer is cellulose. Cellulose containing pads include paper, cloth, woven, or non-woven cellulose substrates. Cloth pads include those containing a natural cellulose fiber such as cotton or wool. Paper pads include those containing natural cellulose fiber (e.g., cellulose or regenerated cellulose) and those containing cellulose fiber derivatives including, but not limited to cellulose esters (e.g., nitrocellulose, cellulose acetate, cellulose triacetate, cellulose proprionate, cellulose acetate propionate, cellulose acetate butyrate, and cellulose sulfate) and cellulose ethers (e.g., methylcellulose, ethylcellulose, ethyl methyl cellulose, hydroxyethyl cellulose, hydroxyethyl methyl cellulose, hydroxypropyl methyl cellulose, ethyl hydroxyethyl cellulose, and carboxymethyl cellulose). In some cases, the cellulose pads contains rayon. In some cases, the pad is paper, such as a variety of WHATMAN® paper.

The bibulous material can also include, but is not limited to, a sintered material. For example, the bibulous material can contain a sintered glass, a sintered polymer, or sintered metal, or a combination thereof. In some cases, the sintered material is formed by sintering one or more of powdered glass, powdered polymer, or powdered metal. In other cases, the sintered material is formed by sintering one or more of glass, metal, or polymer fibers. In still other cases, the sintered material is formed from the sintering of one or more of glass, polymer, or metal beads.

The bibulous material can also contain, but is not limited to, one or more non-cellulosic polymers, e.g. a synthetic polymer, a natural polymer, or a semisynthetic polymer. For example, the material can contain a polyester, such as polyglycolide, polylactic acid, polycaprolactone, polyethylene adipate, polyhydroxylalkanoate, polyhydroxybutyrate, poly(3-hydroxybutyrate-co-3-hydroxyvalerate), polyethylene terephthalate, polybutylene terephthalate, polytrimethylene terephthalate, polyethylene naphthalate, Vectran®. In some cases, the polymer is spunbound, such as a spunbound polyester.

Additional synthetic polymers include, but are not limited to nylon, polypropylene, polyethylene, polystyrene, divinylbenzene, polyvinyl, polyvinyl difluoride, high density polyvinyl difluoride, polyacrylamide, a $(C_2\text{-}C_6)$ monoolefin polymer, a vinylaromatic polymer, a vinylaminoaromatic polymer, a vinylhalide polymer, a $(C_1\text{-}C_6)$ alkyl (meth) acrylate polymer, a(meth)acrylamide polymer, a vinyl pyrrolidone polymer, a vinyl pyridine polymer, a $(C_1\text{-}C_6)$ hydroxyalkyl (meth)acrylate polymer, a (meth)acrylic acid polymer, an acrylamidomethylpropylsulfonic acid polymer, an N-hydroxy-containing $(C_1\text{-}C_6)$ alkyl(meth)acrylamide polymer, acrylonitrile or a mixture of any of the foregoing.

The substrate 112 is generally planar in shape and can be, for example, a membrane formed of nitrocellulose, polyvinylidene fluoride, nylon, or polysulfone. Other materials from which the substrate 112 can be formed include, but are not limited to, glass, plastic, silicon, metal, and/or metal oxide that is bare or is functionalized with polymers. Plastic materials from which the substrate 112 can be formed include, but are not limited to, polyethylene terephthalate, polypropylene, polystyrene, and/or polycarbonate. Examples of polymers with which to functionalize the surface of substrates formed from metal or metal oxide include glycidoxypropyltriethoxysilane, poly-L-lysine, polybrene, polyethylene glycol polymers, dextran polymer, aminopropylsilane, caroxysilane, hydrogels and polymer brushes, and/or self-assembled monolayers of e.g. functionalized alkyl thiols, dendrimers or oligonucleotides.

Exemplary bonding methods to bond all or portions of the wicking pad to the base or cover of the device include, but are not limited to, bonding with an adhesive, thermal bonding, and organic solvent bonding with or without pressure. In embodiments using adhesive, the nature of the adhesive may affect the assay performance (i.e., flow characteristics, reagent stability) and can be optimized for the desired assay or application. In some embodiments, the adhesive may be part of the base 114 of the device 100. Exemplary adhesives include, but are not limited to, spray adhesive, ultraviolet light curable adhesive, or pressure sensitive adhesive.

In some embodiments, the base and/or the cover is formed from plastic including, but not limited to, polyethylene terephthalate, polypropylene, polystyrene, and polycarbonate. The base and/or cover can, for example, be vacuum or injection molded or otherwise constructed. In certain embodiments, the cover is fitted (e.g., snap fitted) to the base. In some embodiments, the cover is molded such that the cover contacts and exerts an even and downward force on the pump when the cover is attached to the base. In certain embodiments, the cover is provided in more than one segment. For example, the cover can include a removable first segment, a second segment and a third segment. The first segment can cover the reservoirs, the second segment can cover the substrate region, and the third segment can cover the pump of the device.

A. Exemplary Detection Reagents i. Binding Agents

Binding agents are described herein for detection of analytes. In some cases, the binding agents are antibodies (e.g., primary or secondary antibodies). Primary antibodies can be used to bind to an analyte. In some cases, the primary antibody is labeled, enabling detection of the primary antibody and subsequent detection of the analyte. In some cases, the primary antibody is detected by binding to a labeled secondary binding agent, such as a labeled secondary antibody. In some cases, tertiary binding agents are utilized to detect complexes containing the analyte and the primary and secondary binding agent.

Binding agents can be provided in one or more reagent solutions. The reagent solutions can contain one of more buffers, salts, density agents, or protein aggregation modifying agents as described herein. Density agents can be used to modulate the viscosity of the reagent solution which will modulate the rate of solution flow out of the reservoirs. Having a density agent in each of the reagent solutions can also enhance binding interactions between, e.g., the analytes immobilized on the substrate and the binding agents (e.g., antibodies). Examples of density agents include, but are not limited to, glycerol, sucrose, trehalose, dextran, and polyethylene glycol. The binding agent(s) can be stored in solution for at least about a day, three days, 7-10 days, at least about a month, two months, 3 months, six months, a year or longer.

Binding agents can also be provided on or in the wicking pad. For example, as illustrated in FIG. 15, lines or spots of binding agents can be immobilized in/on the wicking pad downstream from the reservoir (e.g., in planar region 110). In some embodiments, a first binding agent BA1 is a reversibly immobilized labeled first primary antibody (e.g., a primary antibody conjugate) for detection, a second binding agent BA2 is an irreversibly immobilized unlabeled second primary antibody (e.g., a "test" primary antibody) for capture, and a third binding agent BA3 is a control antibody that binds to the first primary antibody. The control antibody can be used to assess assay validity. In certain embodiments, the labeled first primary antibody is paired with the second primary antibody and the two antibodies bind to different epitopes on the analyte in such a way that the analyte, if present, is sandwiched in between the first primary antibody and second primary antibody during the lateral flow assay. In some embodiments, multiple matched pairs of first and second primary antibodies are immobilized on the wicking pad to allow for multiplex detection of analytes in the sample.

In some cases, a planar region of the wicking pad in fluid communication with fluid in one or more reservoirs contains one or more binding agents dried thereon. The dried binding agent(s) can be reconstituted by contacting the planar region of the wicking pad with an aqueous solution. In some cases, the aqueous reconstitution buffer can contain one or more re-wetting reagents including salts, buffers, or a protein aggregation modifying agent as described herein. In some cases, the binding agent (s) can be stored dry or substantially dry in the wicking pad for at least about a day, three days, 7-10 days, at least about a month, two months, 3 months, six months, a year or longer.

ii. Labels

Analytes can be detected by detecting a label that is linked to a binding agent. The label can be linked directly to the binding agent (e.g., by a covalent or other bond to the primary antibody) or the attachment can be indirect (e.g., using a chelator or linker molecule). The terms "label" and "detectable label" are used synonymously herein. In some embodiments, each label (e.g., a first label linked to a first binding agent, a second label linked to a second binding agent, etc.) generates a detectable signal and the signals (e.g., a first signal generated by the first label, a second signal generated by the second label, etc.) are distinguishable. In some embodiments, the two or more binding agent labels comprise the same type of agent (e.g., a first label that is a first fluorescent agent and a second label that is a second fluorescent agent). In some embodiments, the two or more binding agent labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, colloidal gold, electrochemical labels and combinations thereof. In some embodiments, the label can include an optical agent such as a chromophore, fluorescent agent, phosphorescent agent, chemiluminescent agent, or an electrochemiluminescent agent. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Chromophores include co-enzymes or co-factors that have a detectable absorbance. In some cases, a binding agent can be detected by detecting the intrinsic absorbance of a peptide bond at 220 nm or the composite amino acid absorbance at 280 nm.

Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye, a DyLight dye, or an IRDye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.), Pierce Biotechnology, Inc. (Rockford, Ill.), and Licor Biosciences (Lincoln, Nebr.). In some embodiments, the optical agent is an intercalating dye. In some embodiments, 2, 3, 4, 5, or more binding agents are each labeled with an optical agent such as a fluorescent agent (e.g., a first binding agent labeled with a first fluorescent label, a second binding agent labeled with a second fluorescent label, etc.), and each binding agent that is labeled with an optical agent is detected by detecting a signal generated by the optical agent (e.g., a fluorescent signal generated by a fluorescent label). In some embodiments, the second fluorescent label quenches a fluorescent signal generated by the first fluorescent label. In some embodiments, the first and second fluorescent labels are members of a fluorescence resonance energy transfer (FRET) pair. The term "fluorescence resonance energy transfer" or "FRET" refers to a transfer of energy between at least two chromophores, a donor chromophore and an acceptor chromophore. Typically in FRET, if the donor and acceptor are in sufficiently close proximity, the donor transfers its energy to the acceptor when the donor is excited by light radiation with a suitable wavelength. The acceptor can re-emit the transferred energy in the form of light radiation with a different wavelength. Suitable FRET pairs (donor/acceptor) include, but are not limited to, EDANS/fluorescein, IAEDANS/fluorescein, fluorescein/tetramethylrhodamine, fluorescein/LC Red 640, fluorescein/Cy 5, fluorescein/Cy 5.5, and fluorescein/LC Red 705.

In some embodiments, all of the binding agents are labeled with an optical agent, and each optical agent-labeled binding agent is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cb, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, 2, 3, 4, 5, or more binding agents are each labeled with a radioisotope (e.g., a first binding agent labeled with a first radioisotope, a second binding agent labeled with a second radioisotope, etc.), and each binding agent that is labeled with a radioisotope is detected by detecting radioactivity generated by the radioisotope. For example, one binding agent can be labeled with a gamma emitter and one binding agent can be labeled with a beta emitter. Alternatively, the binding agents can be labeled with radionuclides that emit the same particle (e.g., alpha, beta, or gamma) at different energies, where the different energies are distinguishable. In some embodiments, all of the binding agents are labeled with a radioisotope and each labeled binding agent can be detected by detecting radioactivity generated by the radioisotope.

In some embodiments, the label is an enzyme, and the binding agent is detected by detecting a product generated by the enzyme. Examples of suitable enzymes include, but are not limited to, urease, alkaline phosphatase, (horseradish) hydrogen peroxidase (HRP), glucose oxidase, beta-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm, or a chemiluminescent substrate (e.g., Clarity from Bio-Rad Laboratories), which yields detectable light. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some cases, the enzyme acts on a fluorogenic substrate to generate a detectable fluorescent product. In some embodiments, 2, 3, 4, 5, or more binding agents are each labeled with an enzyme (e.g., a first binding agent labeled with a first enzyme, a second binding agent labeled with a second enzyme, etc.), and each binding agent that is labeled with an enzyme is detected by detecting a product generated by the enzyme. In some embodiments, all of the binding agents are labeled with an enzyme, and each enzyme-labeled binding agent is detected by detecting a product generated by the enzyme.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag, eXact-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length. In some cases, the nucleic acid label is an amplified nucleic acid (e.g, by PCR or by isothermal polymerase extension). In some cases, a label or labels are incorporated into a nucleic acid label using a polymerase, reverse transcriptase, ligase, or other enzymes that act on nucleic acids (eg. fluorescently modified nucleotides, biotin-nucleotides, digoxigenin-nucleotides, hapten nucleotides). In some embodiments, the nucleic acid label is ligated to another label (e.g., a nucleic acid) to create a detectable product (e.g, proximity ligation assays).

In some embodiments, the label is a nucleic acid barcode. As used herein a "barcode" is a short nucleotide sequence (e.g., at least about 4, 6, 8, 10, or 12, nucleotides long) that uniquely defines a labeled molecule, or a second molecule bound to the labeled binding agent. The length of the barcode sequence determines how many unique samples can be differentiated. For example, a 4 nucleotide barcode can differentiate $4^4$ or 256 samples or less, a 6 nucleotide barcode can differentiate 4096 different samples or less, and an 8 nucleotide barcode can index 65,536 different samples or less. The use of barcode technology is well known in the art, see for example Katsuyuki Shiroguchi, et al., "Digital RNA sequencing minimizes sequence-dependent bias and amplification noise with optimized single-molecule barcodes", PNAS 2012 Jan. 24; 109(4):1347-52; and Smith, A M et al., "Highly-multiplexed barcode sequencing: an efficient method for parallel analysis of pooled samples", Nucleic Acids Research 2010 July; 38(13):e142

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectable label (e.g., a fluorescently labeled, biotinylated, or radiolabeled alkyne or azide moiety).

Techniques for attaching detectable labels to binding agents such as proteins (e.g., antibodies) are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

In some embodiments, two or more labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the labeled proteins). Examples of enzymes combining to generate a detectable signal include coupled assays, such as a coupled assay using hexokinase and glucose-6-phosphate dehydrogenase; and a chemiluminescent assay for NAD (P)H coupled to a glucose-6-phosphate dehydrogenase, beta-D-galactosidase, or alkaline phosphatase assay. See, e.g., Maeda et al., *J. Biolumin Chemilumin* 1989, 4:140-148.

B. Protein Aggregation Modifying Agents

Described herein are protein aggregation modifying agents. Protein aggregation modifying agents can be utilized to reduce or eliminate aggregation or denaturation of binding agents, such as proteins (e.g., antibodies), stored in or delivered from a reagent solution, or the wicking pad 102. For example, protein aggregation modifying agents can be utilized to reduce or eliminate aggregation or denaturation of primary antibodies stored in/delivered from the reagent solutions or the wicking pad 102. In some cases, protein aggregation modifying agents can be utilized to facilitate lateral flow of binding agents in the planar region 110 of the wicking pad 102.

In some cases, protein aggregation modifying agents that act to displace proteins from the air-water interface and thereby protect them from denaturation and aggregation are particularly effective in reducing the aggregation of binding agents immobilized on the wicking pad 102. In other cases, the protein aggregation modifying agent directly affects the stability of the binding agent by binding to the binding agent and/or stabilizing the binding agent. In other cases, the protein aggregation modifying agent acts to shift the equilibrium away from a denatured or unfolded state and thus reduce aggregation. For example, in some cases, the interaction between the protein aggregation modifying agent and the binding agent is thermodynamically disfavored due to strong repulsion between an amide backbone of the binding agent and the protein aggregation modifying agent. Thus, unfolding of the binding agent in the presence of the protein aggregation modifying agent is disfavored because unfolding exposes more amide backbone surface to the protein aggregation modifying agent.

Protein aggregation modifying agents can be one or more of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, or a chaotropic agent.

Cyclodextrins can be, but are not limited to, α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy)propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl γ-cyclodextrin, (2,3,6-tri-O-benzoyl)-β-cyclodextrin, succinyl-(2-hydroxypropyl)-β-cyclodextrin, or succinyl-(2-hydroxypropyl)-γ-cyclodextrin. Cyclodextrins can also be a cyclodextrin polymer containing one or more of the foregoing cyclodextrin molecules. Additional cyclodextrins are known in the art, and include, e.g. those described on the world wide web at cyclodextrin.com. Exemplary concentrations of cyclodextrins are, without limitation, about 1 mM, 2 mM, 2.5 mM, 5 mM, 7.5 mM, 10 mM, 15 mM, 20 mM, 25 mM, 50 mM, 75 mM, or 100 mM.

Non-ionic surfactants can be polyethylene-sorbitan-fatty acid esters, polyethylene-polypropylene glycols or polyoxyethylene-stearates. Polyethylene-sorbitan-fatty acid esters can be polyethylene(20)-sorbitan-esters (Tween 20™) or polyoxyethylene(20)-sorbitanmonooleate (Tween 80™). Polyethylene-polypropylene glycols can be polyoxypropylene-polyoxyethylene block co-polymers such as those sold under the names Pluronic® or Poloxamer™. Polyoxyethylene-stearates can be, for example, those sold under the trademark Myrj™. Exemplary, polyoxyethylene monolauryl ethers include those sold under the trademark Brij™, e.g., Brij-35. Exemplary concentrations of non-ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Ionic surfactants can be anionic surfactants or cationic surfactants. Anionic surfactants useful in the present invention can be, but are not limited to, soaps including alkali soaps, such as sodium, potassium or ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride or quarternary ammonium compounds such as benzalkonium chloride. Ionic surfactants can include the sodium, potassium or ammonium salts of alkyl sulfates, such as sodium dodecyl sulfate or sodium octyl sulfate. Exemplary concentrations of ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Zwitterionic surfactants have both cationic and anionic centers attached to the same molecule. The cationic part is, e.g., based on primary, secondary, or tertiary amines or quaternary ammonium cations. The anionic part can be a sulfonate, as in CHAPS (3-[(3-Cholamidopropyl)dimethylammonio]-1-propanesulfonate). Other anionic groups are sultaines illustrated by cocamidopropyl hydroxysultaine or betaines, e.g., cocamidoethyl betaine, cocamidopropyl betaine, or lauramidopropyl betaine. Exemplary concentrations of zwitterionic surfactants are, without limitation, about 0.01%, 0.02%, 0.05%, 0.1%, 0.2%, 0.5%, 0.75%, 1%, 2%, 2.5%, 5%, 7.5%, and about 10% w/w, w/v, or v/v.

Non detergent sulfobetaines (NDSBs) have a sulfobetaine hydrophilic group and a short hydrophobic group that cannot aggregate to form micelles, therefore NDSBs are not considered detergents. Exemplary NDSBs include, but are not limited to NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, or Dimethylethylammoniumpropane sulfonate. Exemplary concentrations of NDSBs include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Polyols are compounds with multiple hydroxyl functional groups. In some cases, polyols can modify the aggregation or denaturation behavior of a protein by a variety of mechanisms. For example, in some cases, the polyol can shift the equilibrium to the folded state by presenting a thermodynamically disfavored interaction with the protein backbone. Alternatively, in some cases, the polyol can bind to and stabilize the folded state of the protein.

Polyols can be simple sugars such as sucrose, mannitol, sorbitol, inositol, xylitol, erythritol, glucose, galactose, raffinose, or trehalose. Polyols can also be polysaccharides such as dextran, starch, hydroxyethyl starch, or polymers containing one or more of the simple sugars described herein. Glycerol, ethylene glycol, polyethylene glycol, pentaerythritol propoxylate, and pentaerythritol propoxylate, and combinations thereof are also exemplary polyols.

Organic solvents can be, but are not limited to, those organic solvent that are known to inhibit denaturation, unfolding, or aggregation of one or more proteins. A variety of suitable organic solvents are known in the art. For example, organic solvents can include ethanol, butanol, propanol, phenol, dimethyl formamide, 2-methyl-2,4-pentanediol, 2,3-butanediol, 1,2-propanediol, 1,6-hexanediol, or dimethyl sulfoxide.

Aggregation modifying proteins can be proteins known in the art to inhibit denaturation, unfolding, or aggregation of one or more proteins. Exemplary aggregation modifying proteins include, but are not limited to, albumins, protein chaperones, and heat shock proteins. Albumins are proteins that are water-soluble, are moderately soluble in concentrated salt solutions, and experience heat denaturation. Exemplary albumins include serum albumins (e.g., bovine, horse, or human serum albumin) or egg albumin (e.g., hen egg-white albumin). Other exemplary aggregation modifying proteins include casein, gelatin, ubiquitin, lysozyme, or late embryogenesis abundant (LEA) proteins. LEA proteins include LEA I, LEA II, LEA III, LEA IV, LEA V, or atypical LEA proteins. LEA proteins are known in the art and described, e.g., in Goyal K., et al., Biochemical Journal 288(pt. 1), 151-57, (2005).

Protein aggregation modifying agents can also be amino acids. In some cases, the amino acids can serve an oxido-reduction function to maintain an appropriate oxidative potential for the protein immobilized on the substrate 112. Suitable oxido-reductive amino acids include cysteine and cystine. Other amino acids serve to reduce denaturation or aggregation through a non-oxido-reductive method. For example, arginine, glycine, proline, and taurine have been shown to reduce protein aggregation.

Other oxido-reduction agents can be employed to reduce protein aggregation. Oxido-reductants other than cysteine and cystine, can be used to optimize the reduction potential in the substrate 112 onto which the protein is immobilized.

Exemplary oxido-reductants include mercaptoethanol, dithiothreitol, dithioerythritol, tris(2-carboxyethyl)phosphine, glutathione, glutathione disulfide, and oxidized derivatives thereof, as well as $Cu^{2+}$.

Protein aggregation modifying agents can also include lyoprotectants, cryoprotectants, or chaotropic agents. In some cases, the protein aggregation modifying agent is a chaotrope such as urea, thiourea, guanidinium, cyanate, thiocyanate, trimethylammonium, tetramethylammonium, cesium, rubidium, nitrate, acetate, iodide, bromide, trichloroacetate, or perchlorate. Under certain conditions, such as at low concentrations, chaotropes can reduce protein aggregation. Other protein aggregation modifying agents include trimethylamine N-oxide.

Protein aggregation modifying agents can be salts. Exemplary salts include, but not limited to, the sodium, potassium, magnesium, or calcium salts of chloride, sulfate, or phosphate. Protein aggregation modifying agents can also be buffering agents. Exemplary buffering agents include, but are not limited to, tris (hydroxymethyl) amino methene (TRIS), TAPSO, MES, HEPES, PIPES, CAPS, CAPSO, MOPS, MOPSO, or sodium or potassium phosphate, carbonate, bicarbonate, citrate, acetate, or borate buffers.

The protein aggregation modifying agents can be provided in any suitable concentration. In some cases, the protein is provided as an aqueous solution containing binding agent and protein aggregation modifying agents. In such cases, the solution can be contacted with the wicking layer and, optionally, dried. Exemplary concentrations of protein aggregation modifying agents in the aqueous binding agent solution include, but are not limited to, about 0.001%, 0.005%, 0.01%, 0.05%, 0.1%, 0.5%, 1%, 2%, 4%, 5%, 10%, 20%, or about 25% or more w/v of the solution. Further exemplary concentrations include, but are not limited to, about 1 µM, 5 µM, 10 µM, 25 µM, 50 µM, 75 µM, 100 µM, 150 µM, 200 µM, 300 µM, 500 µM, 750 µM, 1 mM, 5 mM, 10 mM, 25 mM, 50 mM, 100 mM, 150 mM, 200 mM, 300 mM, 500 mM, and 1M.

In some cases, the protein aggregation modifying agents are provided in the reagent solution. Exemplary compositions containing a protein aggregation modifying agent contain about 0.001%, 0.005%, 0.01%, 0.05%, 0.1%, 0.5%, 1%, 2%, 3%, 4%, 5%, or about 10%, 20%, or about 25% by weight of one or more protein aggregation modifying agents.

Protein aggregation modifying agents can be provided in any suitable combination. For example, in some cases, 1, 2, 3, 4, 5, 6, 7, 8, 9, 10 or more of the foregoing protein aggregation modifying agents can be utilized to reduce aggregation of a binding agent reversibly immobilized on the wicking pad. In some cases, prior to contacting the wicking pad with the binding agent solution, the wicking pad contains a protein aggregation modifying agent, and the binding agent solution contains the same, or a different, protein aggregation modifying agent. In some cases, prior to contacting the wicking pad with the binding agent solution, the wicking pad contains a protein aggregation modifying agent, and the binding agent solution does not contain a protein aggregation modifying agent. In some cases, prior to contacting the wicking pad with the binding agent solution, the binding agent solution contains a protein aggregation modifying agent and the wicking pad, or the region to be contacted, does not.

III. Methods

Provided are methods of performing a lateral flow assay using the devices described herein. In an embodiment, the method comprises contacting a substrate 112 (e.g., a Western blot) having immobilized analytes or binding agent(s) with the wicking pad 102, which can be supplied pre-moistened or can be pre-moistened by the user with, for example, lateral flow buffer. In some embodiments (FIGS. 1-10), the substrate 112 is placed face down on the wicking pad 102 downstream from the reservoirs and upstream from the pump 120 (e.g., between the reservoirs and the pump or in the region 110 of the wicking pad 102). In some embodiments, the substrate is placed on the base such that when a cover is placed onto the device, the wicking pad contacts the substrate 112 in the region 110 of the wicking pad and the substrate 112 is positioned face up relative to the base (FIGS. 11-14).

In embodiments having the wicking pad bonded at least in part to the base (FIGS. 1-10), a different reagent solution is next applied to each of the reservoirs. The reagent solutions can also be applied to the reservoirs in any order. In some embodiments, the reagent solutions are applied to the reservoirs starting with a first reservoir R1 closest to the region 110 for contacting the substrate 112. The reagent solutions can be applied to the reservoirs sequentially or simultaneously. In embodiments having the wicking pad bonded at least in part to the cover (FIGS. 11-14), the different reagent solutions can be applied to each of the reservoirs before or after the cover is placed on the device. In embodiments in which the reagent solutions are applied to the reservoirs after the cover is placed on the device, the solutions can be applied through one or more ports or holes in the device. In an embodiment, four different reagent solutions (e.g., primary antibody, first wash solution, secondary antibodies or secondary detection reagents, and second wash solution) are applied to the reservoirs. In embodiments having two or more sets of reservoirs (FIG. 16), a different or the same set of four reagent solutions is applied to each set of reservoirs, depending on the analytes or binding agents immobilized on the substrate 112.

In some embodiments, a first reagent solution having labeled primary antibody is applied to a first reservoir R1 and a second reagent solution having a first wash solution is applied to a second reservoir R2. In certain embodiments, four different reagent solutions are applied to the reservoirs in the following order: the first reagent solution having primary antibody is applied to the first reservoir R1, the second reagent solution having a first wash solution is applied to the second reservoir R2, a third reagent solution having a secondary antibody or a secondary detection reagent is applied to a third reservoir R3, and a fourth reagent solution having a second wash solution is applied to a fourth reservoir R4. In some embodiments, four different reagent solutions are applied to the reservoirs in the following order: the fourth reagent having the second wash solution is applied to the fourth reservoir R4, the second reagent solution having the first wash solution is applied to the second reservoir R2, the first reagent solution having primary antibody is applied to the first reservoir R1, and the third reagent solution having a secondary antibody or a secondary detection reagent is applied to the third reservoir R3. In certain embodiments, the second reagent solution is applied to the second reservoir R2 before the fourth reagent solution is applied to the fourth reservoir R4. In some embodiments, the reagent solution applied to the reservoir has at least twice the volume of another reagent solution. For example, the volume of the second wash solution in the fourth reservoir R4 can be at least twice the volume of the secondary antibody in the third reservoir R3. In some embodiments, the fourth reagent solution having the second wash solution is omitted to allow the secondary antibody or secondary detection reagent in the third reservoir R3 more time to bind to the primary antibody.

In an embodiment in which the substrate has immobilized binding agents thereon, a sample with an analyte is applied to the first reservoir R1, a first wash solution is applied to the second reservoir R2, a secondary detection reagent is applied to the third reservoir R3 and, if needed, a second wash solution is applied to the fourth reservoir R4.

In some embodiments in which there is no substrate 112 and in which binding agents are immobilized in lines or spots on a planar region 100 of the wicking pad 102 downstream from the reservoirs, a different solution (e.g., a sample or a reagent solution) is applied to at least two of the reservoirs. Referring to FIG. 15, in an embodiment in which a line of labeled reversibly immobilized first primary antibodies (e.g, first binding agent BA1 or primary antibody conjugate), a line of unlabeled irreversibly immobilized second primary antibodies (e.g., second binding agent BA2 or test primary antibodies), and a line of irreversibly immobilized control antibodies (e.g., third binding agent BA3) that bind to the first primary antibodies is printed on the planar region 110 of the wicking pad 102, a sample having one or more analytes and optionally a control protein is applied to the first reservoir R1 and a wash solution (e.g., lateral flow buffer) is applied to the second reservoir R2. In some embodiments in which an unlabeled second primary antibody and a control antibody are irreversibly immobilized on the planar region 110 of the wicking pad 102, a detection reagent (e.g., labeled primary antibody) is applied to the third reservoir R3 and, if needed, a second wash solution is applied to the fourth reservoir R4.

In an embodiment in which analytes are immobilized in lines or spots on the planar region 110 of the wicking pad 102 downstream from the reservoirs, a labeled primary antibody is applied to the first reservoir R1 and a first wash solution is applied to the second reservoir R2. If needed, a secondary detection reagent is applied to the third reservoir R3 and a second wash solution is applied to the fourth reservoir R4.

The reagent solutions and/or sample are then allowed to flow sequentially from the reservoirs onto the region 110 of the wicking pad 102. In an embodiment having reagent immobilized in a zone of the wicking pad 102 inside one or more of the reservoirs, to initiate sequential flow of the reagents from the reservoirs to the wicking pad 102, lateral flow (e.g., running) buffer is applied sequentially or simultaneously to all of the reservoirs. In some cases, the lateral flow (e.g., the progress) of each of the reagent solutions out of the reservoirs 116 and into/through the wicking pad 102 is monitored visually with one or more dyes or indicators in each of the reagent solutions.

In embodiments having analytes immobilized on the substrate 112, the reagent solutions are pulled by wicking from the reservoirs into the wicking pad and to the dry pump, carrying the reagents (e.g., the primary antibody, the first wash solution, and if needed, secondary antibodies and the second wash solution) in the reagent solutions sequentially by lateral flow into contact with the substrate 112 having proteins or analytes immobilized thereon. The primary antibodies in the first reagent solution are transported in the wicking pad 102, contact the proteins or analytes on the substrate 112, and bind to the target proteins or analytes, if present, on the substrate 112. In some embodiments, lateral flow of the reagent solutions/lateral flow buffer from the reservoirs to the pump further allows the first wash solution in the second reagent solution to be transported in the wicking pad 102 such that unbound primary antibodies are removed from the substrate 112. In certain embodiments, lateral flow of the reagent solutions/lateral flow buffer from the reservoirs to the pump further allows the secondary antibodies or a secondary detection reagent in the third reagent solution to be transported in the wicking pad 102 and to contact the primary antibodies bound to their target proteins, if present, on the substrate 112. In some embodiments, lateral flow of the reagent solutions/lateral flow buffer from the reservoirs to the pump further allows the second wash solution in the fourth reagent solution to be transported in the wicking pad 102 such that unbound secondary antibodies are removed from the substrate 112. In some embodiments, the volume of the second wash solution applied to and transported in the wicking pad 102 is twice the volume of secondary antibody applied to and transported in the wicking pad 102.

In embodiments in which binding agents are immobilized on the substrate 112, the sample and reagent solutions are pulled by wicking from the reservoirs into the wicking pad and to the dry pump, carrying the analytes (and optional control protein) in the sample and the reagents (e.g., the first wash solution, the secondary detection reagent and, if needed, the second wash solution) in the reagent solutions sequentially by lateral flow into contact with the substrate 112. In some embodiments, the sample is a biological sample. Biological samples can be obtained from any biological organism, e.g., an animal, plant, fungus, bacterial, or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, transformed cells, stem cells, stool, or urine. In some embodiments, the sample includes a positive control protein for assessing assay validity or for normalizing the test signal across a multiplicity of different antibody zones.

In embodiments in which binding agents are immobilized on the region 110 of the wicking pad downstream from the reservoirs, the sample and reagent solutions are pulled by wicking from the reservoirs into the wicking pad and to the dry pump, carrying the analytes in the sample and the reagents (e.g., the first wash solution and, if needed, the secondary detection reagent and the second wash solution) in the reagent solutions sequentially by lateral flow into contact with the region 110.

In some embodiments, before or after initiating lateral flow and during lateral flow, a substantially uniform pressure is applied to the pump to improve contact of the pump with the wicking pad 102. For example, a weight can be placed on top of the pump or the cover (or a portion of the cover) can be attached to the base to urge the pump toward the wicking pad 102.

In embodiments having the wicking pad bonded at least in part to the base, a cover can be placed onto the device once the reagent solutions have been applied to the reservoirs to minimize evaporation and to apply even pressure to the pump 120. The cover can be snap-fit onto the base to apply even pressure or the cover can be placed loosely on top of the base and then the base with the cover can be placed into a drawer-like container that slides into a box. Prior to attaching the cover or in place of the cover, a sponge can be placed on the pump to aide in applying even pressure to the pump. The process requires minimal user interaction with the consumable.

In some embodiments having a substrate, during lateral flow, the binding of primary antibodies to the target proteins (and optionally contact of secondary antibodies or secondary detection reagents to the primary antibody) is followed visually or by using a detector. In some embodiments, the substrate 112 is removed from the lateral flow device 100 and the binding of the primary antibodies to the target proteins, if present, is detected. In some embodiments, the antibody binding to the target protein is visualized and/or detected through the use of detectable moieties and/or labels as described herein. Suitable labels and/or moieties are detected by spectroscopic, photochemical, biochemical, immunochemical, isotopic, electrical, optical, chemical, or mass spectrometric techniques.

In an embodiment in which binding agents are immobilized on the planar region 110 of the wicking pad, during lateral flow, the binding of the analyte, if present, to the first primary antibody and to the second primary antibody (e.g., detection of the analyte sandwiched between the first and second primary antibodies) is followed visually or by using a detector. In some embodiments, the binding of the analyte to the first and second primary antibodies is visualized and/or detected through the use of detectable moieties and/or labels as described herein.

There are many absorbent bibulous pad materials, wick pad materials, and antibody application materials known in the art, the selection from which can be made to control the volume, to control the flow rate of the system, to ensure even flow, and to ensure complete delivery of antibodies/reagents from the reservoirs. Other methods that affect the timing of reagent/antibody delivery such as using torturous paths in the wick pad are possible. Still other embodiments to control the lateral flow process could be engineered into the plastic casing where the surface may contain sloped regions to slow or speed the flow of liquid using gravity (see FIGS. 2 and 3).

Shown in FIGS. 1-15 are consumable devices that hold a single mini-gel sized membrane. Often users run western blots using membranes termed midi size blots which are typically 2× the width of a mini sized membrane. In other western blot applications the user may cut a mini and/or midi sized membrane into smaller sections that correspond to a few lanes of the original gel used for electrophoresis and transfer of the proteins. Therefore, the consumable lateral flow device could be of a size to accommodate either a mini or midi-sized membrane in some embodiments. In still other embodiments there could be separate ridges molded into or otherwise present in the base of the consumable where membrane sections could be placed.

In other embodiments of the lateral flow device, multiple antibodies may be mixed and loaded into one or more of the reservoirs to facilitate multiplex detection of targets in a single sample.

IV. Kits

Kits for performing a lateral flow assay according to methods described herein are provided. Also provided are kits containing lateral flow devices as described herein. In some embodiments, the kit comprises reagents (e.g., binding agents including labeled primary antibody or primary and secondary antibodies, wash solution, and/or lateral flow buffer) in liquid form (e.g., reagent solutions) that are applied to the device by the end-user. In some embodiments, solutions are provided in a concentrated form (e.g., 5× or 10×) that is diluted prior to use. In some embodiments, the reagents are provided in solid form that is reconstituted with liquid, e.g. buffer, prior to use.

In some embodiments, the kit contains blocking agents (e.g., bovine serum albumin and/or non-fat dried milk), surfactants (e.g., Tween 20 or Triton X-100), protein aggregation modifying agents as described herein, crowding agents (e.g., dextran, polyethylene glycol and/or Ficoll), density agents, and/or agents to promote even flow of reagents and/or promote reaction to molecules on the substrate and minimize background on the substrate. The additional agents can be provided in the kit as a solid (e.g., a powder) or in liquid form (e.g., as a solution). In some embodiments, the kit further comprises instructions for carrying out the methods described herein.

IV. Examples

Example 1—Sequential Lateral Flow of Solutions from Reservoirs

This example illustrates the sequential lateral flow of colored solutions from reservoirs in a lateral flow device as depicted in FIGS. 4A and 4B.

Figure 17A:
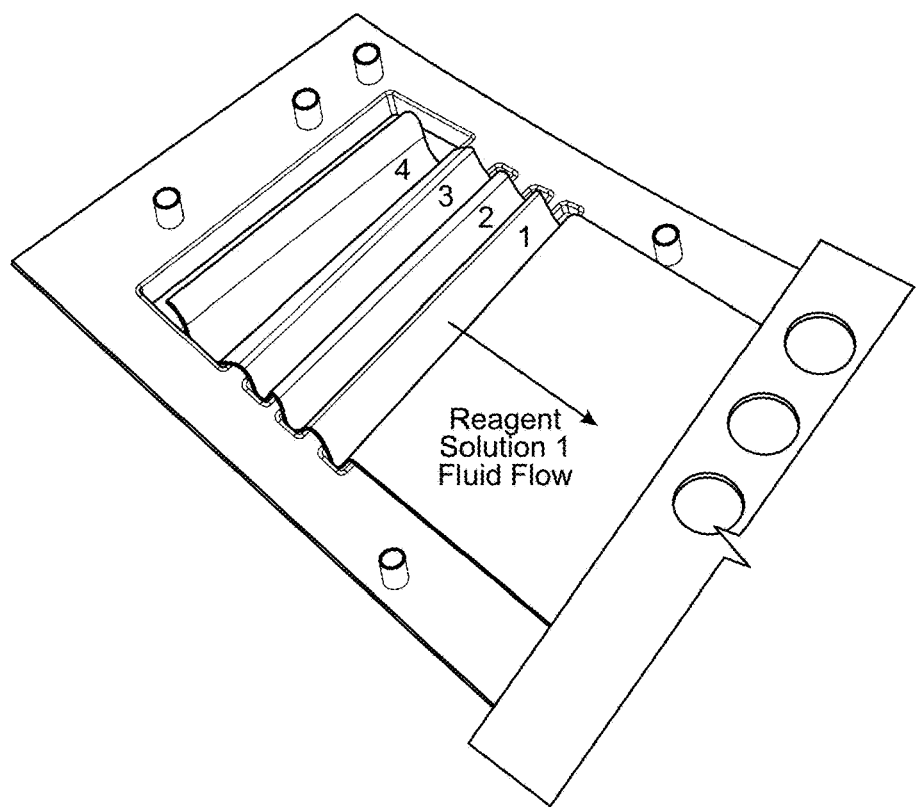
FIGS. 17A-17E are perspective views of the lateral flow device of FIGS. 4A and 4B during various stages of operation and as described in Example 1. The solutions emptied from the reservoirs into the wicking pad in sequential order starting at reservoir 1 and ending with reservoir 4. The portion of the device having the pump is not shown in the views.
Figure 17B:
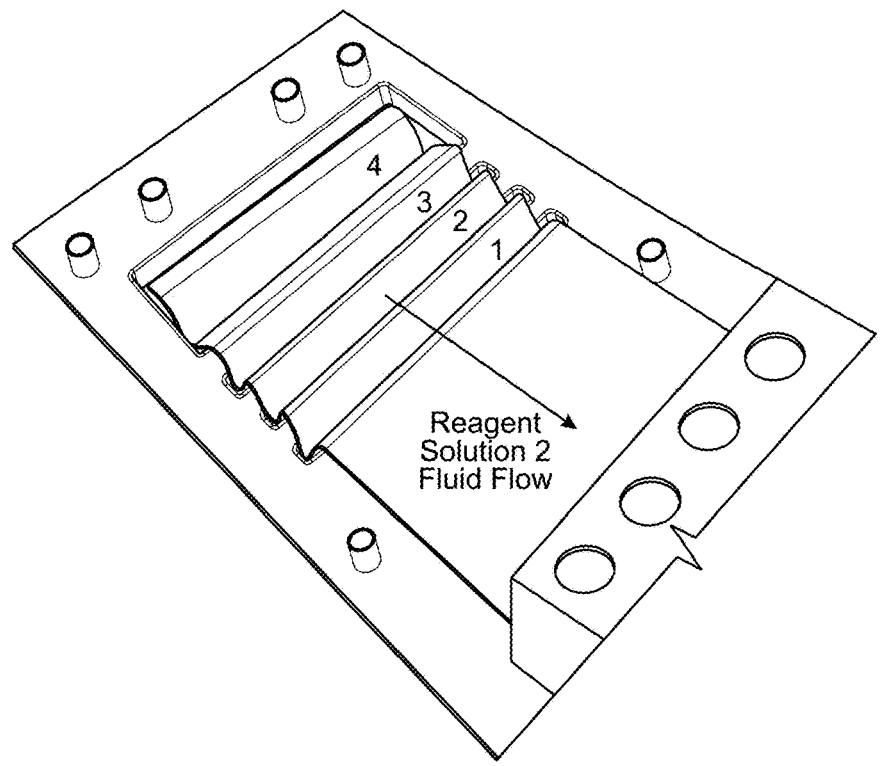
Figure 17C:
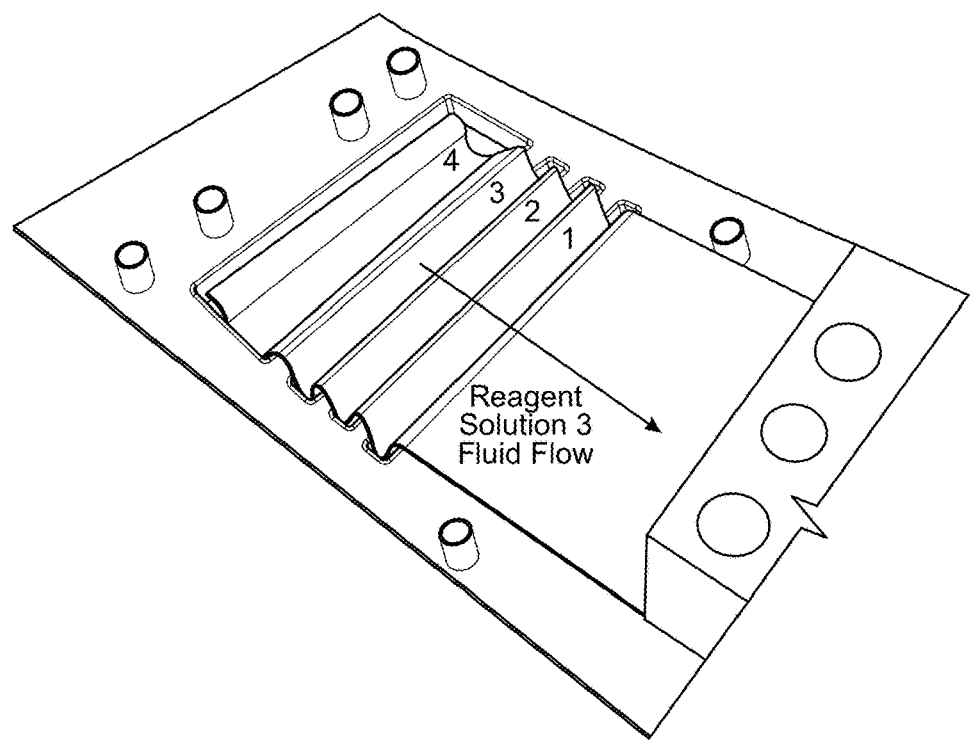
Figure 17D:
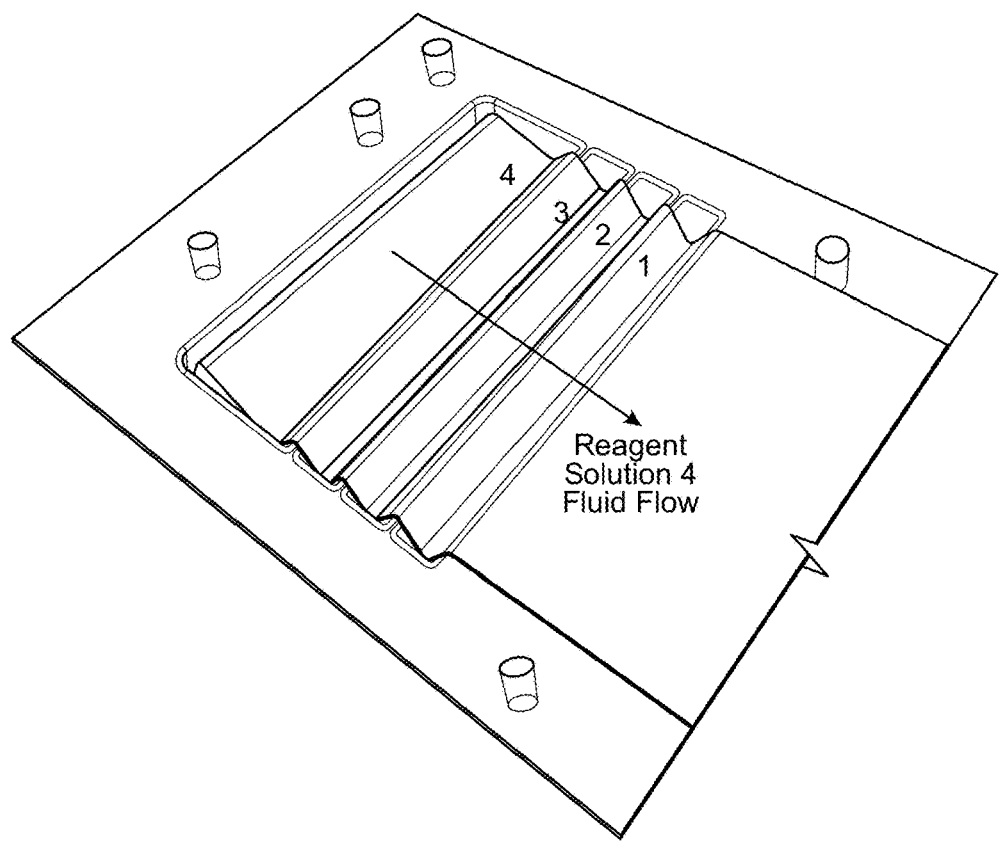
Figure 17E:
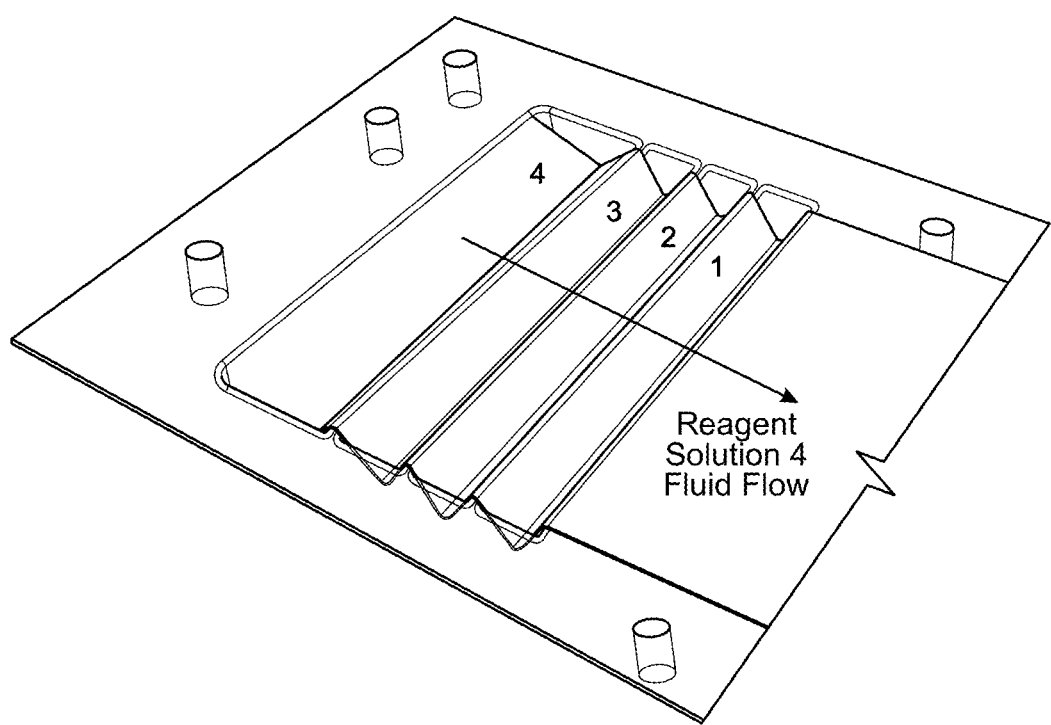

In FIG. 17A, the wick pad (glass fiber) was wet first with lateral flow buffer (1% casein, 1×PBS Buffer, 0.1% Tween 20), a pump (not shown in FIGS. 17A-17E, see FIG. 4A) was placed on the right side of the device. Yellow and blue dye solutions were made by adding Orange G (Sigma) or Xylene Cyanol (Bio-Rad) to lateral flow buffer. Alternating yellow and blue solutions were placed into reservoirs R1, R2, R3 and R4. Solution 1 in reservoir 1 flowed into and was completely drained into the wicking pad as the solution 1 was drawn to the pump (FIG. 17B). While the solution 1 was flowing into the wicking pad, the solutions 2, 3, and 4 in the other reservoirs did not move nor mix. As shown in FIG. 17C, after solution 1 was completely drained from the reservoir 1, the solution 2 in Reservoir 2 migrated by lateral flow out of Reservoir 2 through the wick material, across the upstream wall of Reservoir 1 and up the downstream wall in its flow course to the pump. Again, the solutions remaining in the reservoirs most distant to the pump (R3 and R4) did not empty or mix. Once the solution 2 was completely drained from the reservoir 2, the liquid in the reservoir 3 was then drained by the pump (FIG. 17D). Lastly, as shown in FIG. 17E, the solution in Reservoir 4 was partially depleted as the solution flowed to the pump. After some time, the Reservoir 4 was completely drained (not shown).

The results show that the lateral flow devices described herein can deliver solutions sequentially to a wicking pad.

Example 2—Detection of hRAS, PCNA and PARP from HEK293 Cell Lysate

This example illustrates the use of lateral flow devices as depicted in FIGS. 4A and 4B and as described herein to perform western blot assays.

Lyophilized HEK293 protein lysate (Bio-Rad Laboratories PrecisionAb control lysate VLY002) was reconstituted in 1× Laemmli sample buffer containing 40 mM DTT and denatured by heating at 100° C. for 5 min. A series of two-fold dilutions of the lysate (20 ug down to 0.04 ug) was loaded onto 4-20% TGX mini gels (Bio-Rad Laboratories) and electrophoresed at 250V for 25 min. Each gel was transferred to a PVDF membrane using the Transblot Turbo device (Bio-Rad) and prepacked transfer packs using a setting of 2.5 A×7 min per two gels. Following transfer, the membranes were quickly rinsed in 1×PBS buffer (10 mM sodium phosphate, 150 mM NaCl, pH 7.4) and then placed in a lateral flow buffer containing 1% casein, 1×PBS Buffer, 0.1% Tween 20, and placed on a rocker for 10 minutes to block. While the membranes were incubating in lateral flow buffer, three primary antibody solutions were prepared at a 1:1000 dilution by mixing 3 µl of (1) mouse anti-hRAS monoclonal Ab (Bio-Rad Laboratories, # VMA00040), (2) mouse anti-PCNA monoclonal Ab (Bio-Rad Laboratories, # VMA00018), and (3) mouse anti-PARP monoclonal Ab (Bio-Rad Laboratories, # VMA00016) into 3 ml of lateral flow buffer. Secondary antibody (goat anti-mouse IgG-HRP antibody conjugate, Bio-Rad Laboratories # STAR207P) was prepared at a 1:1000 dilution in lateral flow buffer.

Blot detection was performed as follows. A glass fiber wick pad (Ahlstrom) was cut to 8.4 cm×21 cm and thermally bonded to the v-shaped contour of the tray during the vacuum molding process as shown in FIGS. 4A and 4B. Nine layers of thick blot paper ~4.3 cm×9.5 cm (Bio-Rad) were placed on one end of the wick pad to serve as the pump. The glass fiber wick pad was wet with 7 ml of lateral flow buffer. The membrane was removed from blocking solution, and placed inverted (antigen side down) onto the wicking pad with the low molecular weight proteins nearest the pump; bubbles were removed by rolling. A 0.7 kg mass was placed atop the pump to ensure uniform contact with the wicking pad, and then the troughs, as numbered in FIGS. 17A-17E, were immediately filled with reagent solutions (Reservoir 1: 3 ml of primary antibody; Reservoir 2: 3 ml of lateral flow buffer; Reservoir 3: 2 ml of secondary antibody; and Reservoir 4: 8 ml of lateral flow buffer). The lateral flow devices were left on a level surface at room temperature undisturbed until all the reservoirs were drained of liquid.

After 4 hours, the membranes were removed from the lateral flow devices and washed 2×5 minutes in water. Detection of the binding reaction between the antigens and binding agents was performed using Clarity chemiluminescent substrate (Bio-Rad Laboratories) per the instructions. FIGS. 18A, 18B and 18C are images of the three blot membranes corresponding to the three antigens (hRAS, PCNA, and PARP) tested. The images shown in FIGS. 18A-18C were acquired using Bio-Rad's Chemidoc MP imager using exposure times of 14 seconds for FIG. 18A, 1 second for FIG. 18B, and 46 seconds for FIG. 18C. The images show that all three target antigens were detected at multiple dilutions of the HEK293 cell lysate.

The results show that the lateral flow devices described herein can deliver western blotting reagents (e.g., specific binding agents, lateral flow buffer, wash solutions) sequentially and without user intervention to a blot on a wicking pad.

All patents, patent applications, and other published reference materials cited in this specification are hereby incorporated herein by reference in their entirety.

What is claimed is:

1. A lateral flow device comprising:
   a wicking pad composed of a porous material, the wicking pad having a planar region for contacting a substrate comprising immobilized analytes; and
   wherein the wicking pad has a first end, a second end and two lateral edges;
   a base comprising two or more reservoirs having top openings that are spatially separated from each other by reservoir walls, wherein each of the reservoirs receives and is in fluid communication with the first end of the wicking pad, wherein the first end of the wicking pad is received from the top openings of each reservoir and passes over the reservoir walls;
   a pump comprising an absorbent pad contacting the second end of the wicking pad; and
   a cover covering the base,
   wherein at least two portions of the wicking pad are formed into protrusions each of which project into a different reservoir when the cover is placed onto the device; and
   wherein at least a part of the wicking pad is bonded to the cover.

2. The device of claim 1, wherein the cover is attached to the base.

3. The device of claim 2, wherein the wicking pad is bonded to the cover in the planar region that contacts the substrate.

4. The device of claim 1, wherein each of the reservoirs is a depression.

5. The device of claim 1, wherein each reservoir has a longest dimension perpendicular to the lateral edges of the wicking pad.

6. The device of claim 1, wherein a lowest point of one or more of the reservoirs is located below the plane of the planar region for contacting the substrate.

7. The device of claim 1, wherein each of the reservoirs spans a width of the wicking pad.

8. The device of claim 1, wherein a cross-section of each of the reservoirs has a shape selected from the group consisting of a v, a semicircle, an oval, a u, a rectangle, a square, and a trapezoid.

9. The device of claim 1, wherein the reservoirs are attached to each other on at least one side.

10. The device of claim 1, wherein the pump contacts an upper surface or a lower surface of the second end of the wicking pad.

11. A method of performing a lateral flow assay, the method comprising;
   providing the device of claim 1;
   removing the cover from the base;
   optionally applying a lateral flow buffer to the wicking pad;
   contacting the substrate comprising proteins to the planar region of the wicking pad for contacting the substrate;
   applying a different reagent solution to each of the reservoirs starting with a reservoir closest to the planar region for applying the substrate;
   contacting each reagent solution with the first end of the wicking pad by placing the cover on the base and dipping at least two protrusions formed in different portions of the first end of the wicking pad into the reagent solutions; and
   allowing lateral flow of the reagent solutions from the reservoirs to the pump such that each of the reagents in the reagent solutions is sequentially transported in the wicking pad and is contacted to the proteins on the substrate.

12. A method of performing a lateral flow assay, the method comprising;
   providing the device of claim 1;
   removing the cover from the base;
   optionally applying a lateral flow buffer to the wicking pad;
   contacting the substrate comprising proteins to the planar region of the wicking pad for contacting the substrate;
   positioning the cover on the base, thereby placing a protrusion formed from the first end of the wicking pad into each of the reservoirs;

applying a different reagent solution to each of the reservoirs starting with a reservoir closest to the planar region for applying the substrate such that each reagent solution contacts different portions of the first end of the wicking pad; and allowing lateral flow of the reagent solutions from the reservoirs to the pump such that each of the reagents in the reagent solutions is sequentially transported in the wicking pad and is contacted to the proteins on the substrate.

13. The method of claim 11, wherein the contacting the substrate comprising proteins to the planar region of the wicking pad comprises contacting an upper surface or a lower surface of the wicking pad.

14. The method of claim 12, wherein the applying a different reagent solution to each of the reservoirs step comprises applying the reagent solution through a port in each of the reservoirs or in the cover.

15. The method of claim 11, wherein the allowing lateral flow step comprises allowing primary antibodies from a first reagent solution in a first reservoir to bind to their target proteins, if present, on the substrate, followed by allowing a first wash solution from a second reagent solution in a second reservoir to remove unbound primary antibodies from the substrate.

16. The method of claim 15, wherein the allowing lateral flow step further comprises allowing secondary antibodies or a secondary detection reagent from a third reagent solution in a third reservoir to contact the primary antibodies bound to their target proteins, if present, on the substrate.

17. The method of claim 16, wherein the allowing lateral flow step further comprises allowing a second wash solution from a fourth reagent solution in a fourth reservoir to remove unbound secondary antibodies from the substrate.

18. The method of claim 17, wherein a volume of the second wash solution is at least twice a volume of the third reagent solution having the secondary antibody.

19. The method of claim 11, further comprising applying a substantially uniform pressure to the pump.

20. The method of claim 11, further comprising detecting the binding of the primary antibodies to the target proteins if present.

* * * * *